United States Patent
Surana et al.

(10) Patent No.: US 12,414,971 B2
(45) Date of Patent: Sep. 16, 2025

(54) METHODS AND COMPOSITIONS TO TREAT AND PREVENT INFECTION

(71) Applicants: DUKE UNIVERSITY, Durham, NC (US); PRESIDENT AND FELLOWS OF HARVARD COLLEGE, Cambridge, MA (US); CHILDREN'S MEDICAL CENTER CORPORATION, Boston, MA (US)

(72) Inventors: Neeraj K. Surana, Durham, NC (US); Dennis Kasper, Cambridge, MA (US)

(73) Assignees: DUKE UNIVERSITY, Durham, NC (US); PRESIDENT AND FELLOWS OF HARVARD COLLEGE, Cambridge, MA (US); CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 17/279,386

(22) PCT Filed: Sep. 25, 2019

(86) PCT No.: PCT/US2019/052895
§ 371 (c)(1),
(2) Date: Jan. 7, 2022

(87) PCT Pub. No.: WO2020/068936
PCT Pub. Date: Apr. 2, 2020

(65) Prior Publication Data
US 2021/0386799 A1 Dec. 16, 2021

Related U.S. Application Data

(60) Provisional application No. 62/736,114, filed on Sep. 25, 2018.

(51) Int. Cl.
*A61K 35/747* (2015.01)
*A23L 33/135* (2016.01)

(52) U.S. Cl.
CPC .......... *A61K 35/747* (2013.01); *A23L 33/135* (2016.08); *A23V 2400/173* (2023.08)

(58) Field of Classification Search
CPC ... A61K 35/747; A61K 35/744; A23L 33/135; A23V 2400/173; A61P 31/04
See application file for complete search history.

(56) References Cited

U.S. PATENT DOCUMENTS

| | | | |
|---|---|---|---|
| 5,439,678 | A | 8/1995 | Dobrogosz et al. |
| 10,376,563 | B1 | 8/2019 | Van Pijkeren et al. |
| 2012/0027736 | A1 | 2/2012 | Morita et al. |
| 2015/0306156 | A1 | 10/2015 | Borody |
| 2016/0120915 | A1 | 5/2016 | Blaser et al. |

FOREIGN PATENT DOCUMENTS

| | | |
|---|---|---|
| EP | 2674162 A1 | 12/2013 |
| WO | 2010124387 A1 | 11/2010 |
| WO | 2014145958 A2 | 9/2014 |

OTHER PUBLICATIONS

Natividad et al., Applied and environmental Microbiolgy, 2013, vol. 79, No. 24, p. 7745-7754doi:10.1128/AEM.02470-13. (Year: 2013).*
Kim et al., Intest Res. Jan. 2014;12(1):20-33. doi: 10.5217/ir.2014.12.1.20.Epub Jan. 28, 2014. PMID: 25349560; PMCID: PMC4204685. (Year: 2014).*
Huang et al., Front. Immunol., Sep. 3, 2017, Sec. Microbial Immunology, vol. 8—2017; doi.org/10.3389/fimmu.2017.01063. (Year: 2017).*
Acton et al, "Intestinal carriage of *Staphylococcus aureus*: how does its frequency compare with that of nasal carriage and what is its clinical impact?" European Journal of Clinical Microbiology & Infectious Diseases, Feb. 2009, pp. 125-127, 28.
Boyce et al, "Frequency and possible infection control implications of gastrointestinal colonization with methicillin-resistant *Staphylococcus aureus*," Journal of Clinical Microbiology, Dec. 2005, pp. 5992-5995, 43(12).
Brandl et al, "Vancomycin-resistant enterococci exploit antibiotic-induced innate immune deficits," Nature, Oct. 2008, pp. 804-807, 455.
Cash et al, "Symbiotic bacteria direct expression of an intestinal bactericidal lectin," Science, Aug. 2006, pp. 1126-1130, 313(5790).
Choi et al, "Innate Stat3-mediated induction of the antimicrobial protein Reg3γ is required for host defense against MRSA pneumonia," Journal of Experimental Medicine, Mar. 2013, pp. 551-561, 210(3).
Chung et al, "Gut immune maturation depends on colonization with a host-specific microbiota," Cell, Jun. 2012, pp. 1578-1593, 149(7).
Darnaud et al, "Enteric Delivery of Regenerating Family Member 3 alpha Alters the Intestinal Microbiota and Controls Inflammation in Mice With Colitis," Gastroenterology, Mar. 2018, pp. 1009-1023, 154(4).
Geva-Zatorsky et al, "Mining the Human Gut Microbiota for Immunomodulatory Organisms," Cell, Feb. 2017, pp. 928-943, 168(5).
International Searching Authority, International Search Report and Written Opinion for corresponding International Application PCT/US2019/052895, mailed Dec. 17, 2019, 4 pages.
Islam et al, "Downregulation of bactericidal peptides in enteric infections: a novel immune escape mechanism with bacterial DNA as a potential regulator," Nature Medicine, Feb. 2001, pp. 180-185, 7(2).
Jones et al, "Probiotic Lactobacillus reuteri Biofilms Produce Antimicrobial and Anti-inflammatory Factors," BMC Microbiology, Dec. 2009, pp. 1-9, 9.

(Continued)

*Primary Examiner* — Kade Ariani
(74) *Attorney, Agent, or Firm* — Quarles & Brady, LLP

(57) ABSTRACT

In certain aspects, described herein are methods, bacteria, and compositions for the treatment of bacterial infections. Specifically, bacteria that can upregulate antimicrobial peptides, e.g., Reg3, within a subject have been identified and methods of using such bacteria to treat infections is described.

13 Claims, 12 Drawing Sheets

(56) References Cited

OTHER PUBLICATIONS

Kandler et al, "*Lactobacillus reuteri* sp. Nov., a New Species of *Heterofermentative lactobacilli*," Zentralblatt Für Bakteriologie: I. Abt. Originale C: Allgemeine, Angewandte Und Ökologische Mikrobiologie, Sep. 1980, pp. 264-269, 1(3).
Lehotzky et al, "Molecular basis for peptidoglycan recognition by a bactericidal lectin," Proceedings of the National Academy of Sciences, Apr. 2010, pp. 7722-7727, 107(17).
Mazmanian et al, "An immunomodulatory molecule of symbiotic bacteria directs maturation of the host immune system," Cell, Jul. 2005, pp. 107-118, 122(1).
Miki et al, "The bactericidal activity of the C-type lectin RegIIIbeta against Gram-negative bacteria involves binding to lipid," Journal of Biological Chemistry, Oct. 2012, pp. 34844-34855, 287(41).
Misawa et al, "*Staphylococcus aureus* Colonization of the Mouse Gastrointestinal Tract Is Modulated by Wall Teichoic Acid, Capsule, and Surface Proteins," PLoS pathogens, Jul. 2015, 11(7):e1005061.
Mukherjee et al, "Regulation of C-type lectin antimicrobial activity by a flexible N-terminal prosegment," Journal of Biological Chemistry, Feb. 2009, pp. 4881-4888, 284(8).
Mukherjee et al, "Antibacterial membrane attack by a pore-forming intestinal C-type lectin," Nature, Jan. 2014, pp. 103-107, 505(7481).
Mukherjee et al, "Antimicrobial defense of the intestine," Immunity, Jan. 2015, pp. 28-39, 42(1).
Pai et al, "Transplantation outcomes for severe combined immunodeficiency, 2000-2009," New England Journal of Medicine, Jul. 2014, pp. 434-446, 371(5).
Peng et al, "Update on Antimicrobial Resistance in Clostridium difficile: Resistance Mechanisms and Antimicrobial Susceptibility Testing. Journal of Clinical Microbiology," Journal of Clinical Microbiology, Apr. 2017, pp. 1998-2008, 55 (7).
Peschel et al, "Inactivation of the dit operon in *Staphylococcus aureus* confers sensitivity to defensins, protegrins, and other antimicrobial peptides," Journal of Biological Chemistry, Mar. 1999, pp. 8405-8410, 274(13).
Peters et al, "Antimicrobial peptides: primeval molecules or future drugs?" PLoS pathogens, Oct. 2010, 6(10):e1001067.
Robey et al, "Identification of Legionella pneumophila rcp, a pagP-like gene that confers resistance to cationic antimicrobial peptides and promotes intracellular infection," Infection and Immunity, Jul. 2001, pp. 4276-4286, 69(7).
Rubio et al, "The Natural Antimicrobial Enzyme Lysozyme is Up-Regulated in Gastrointestinal Inflammatory Conditions," Pathogens, Jan. 2014, pp. 73-92, 3(1).
Sadighi Akha et al, "Acute infection of mice with Clostridium difficile leads to eIF2α phosphorylation and pro-survival signalling as part of the mucosal inflammatory response," Immunology, Sep. 2013, pp. 111-122, 140(1).
Shintani et al, "Validation of Sterilization Procedures and Usage of Biological Indicators in the Manufacture of Healthcare Products," Biocontrol Science, 2011, pp. 85-94, 16(3).
Sieprawska-Lupa et al, "Degradation of human antimicrobial peptide LL-37 by *Staphylococcus aureus*-derived proteinases," Antimicrobial agents and Chemotherapy, Dec. 2004, pp. 4673-4679, 48(12).
Stelter et al, "*Salmonella*-induced mucosal lectin RegIIIβ kills competing gut microbiota," PLoS One, Jun. 2011, 6(6):e20749.
Surana et al, "Moving beyond microbiome-wide associations to causal microbe identification," Nature, Dec. 2017, pp. 244-247, 552(7684).
Ubeda et al, "Vancomycin-resistant Enterococcus domination of intestinal microbiota is enabled by antibiotic treatment in mice and precedes bloodstream invasion in humans," The Journal of Clinical Investigation, Dec. 2010, pp. 4332-4341, 120(12).
Vaishnava et al, "Paneth cells directly sense gut commensals and maintain homeostasis at the intestinal host- microbial interface," Proceedings of the National Academy of Sciences, Dec. 2008, pp. 20858-20863, 105(52).
Vaishnava et al, "The antibacterial lectin RegIIIgamma promotes the spatial segregation of microbiota and host in the intestine," Science, Oct. 2011, pp. 255-258, 334(6053).
Van Ampting et al, "Intestinally secreted C-type lectin Reg3b attenuates salmonellosis but not listeriosis in mice," Infection and Immunity, Mar. 2012, pp. 1115-1120, 80(3).
Wang et al, "Intestinal REG3 Lectins Protect against Alcoholic Steatohepatitis by Reducing Mucosa-Associated Microbiota and Preventing Bacterial Translocation," Cell Host Microbe, Feb. 2016, pp. 227-239, 19(2).
Winer et al, "The Intestinal Immune System in Obesity and Insulin Resistance," Cell Metabolism, Mar. 2016, pp. 413-426, 23.
Zhao et al, "Survival signal REG3a prevents crypt apoptosis to control acute gastrointestinal graft-versus-host disease," The Journal of Clinical Investigation, Sep. 2018, pp. 4970-4979, 128(11).

\* cited by examiner

Figure 1
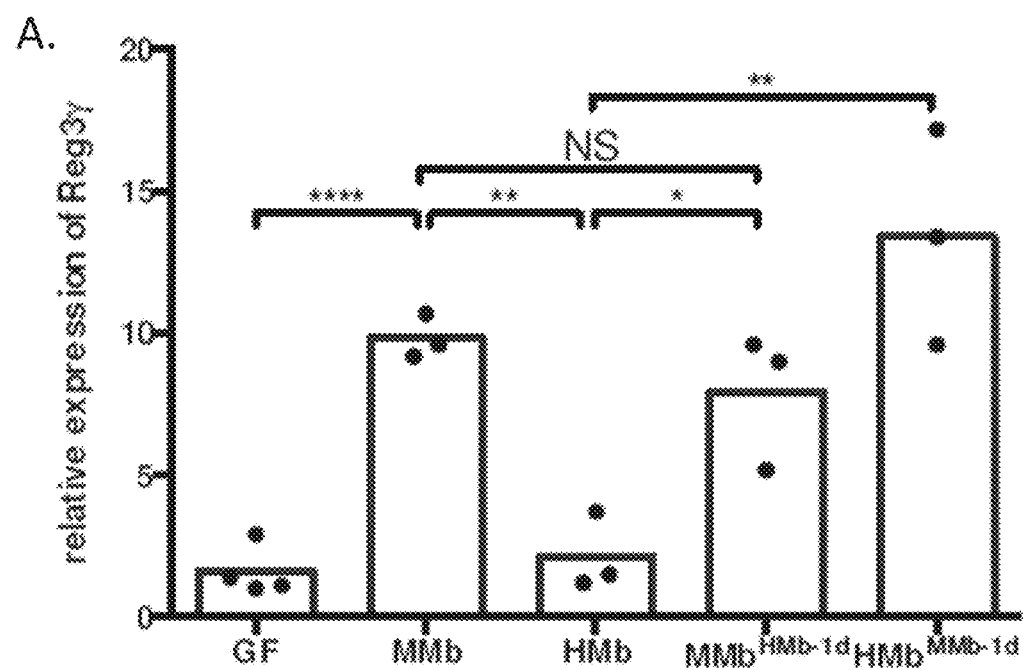
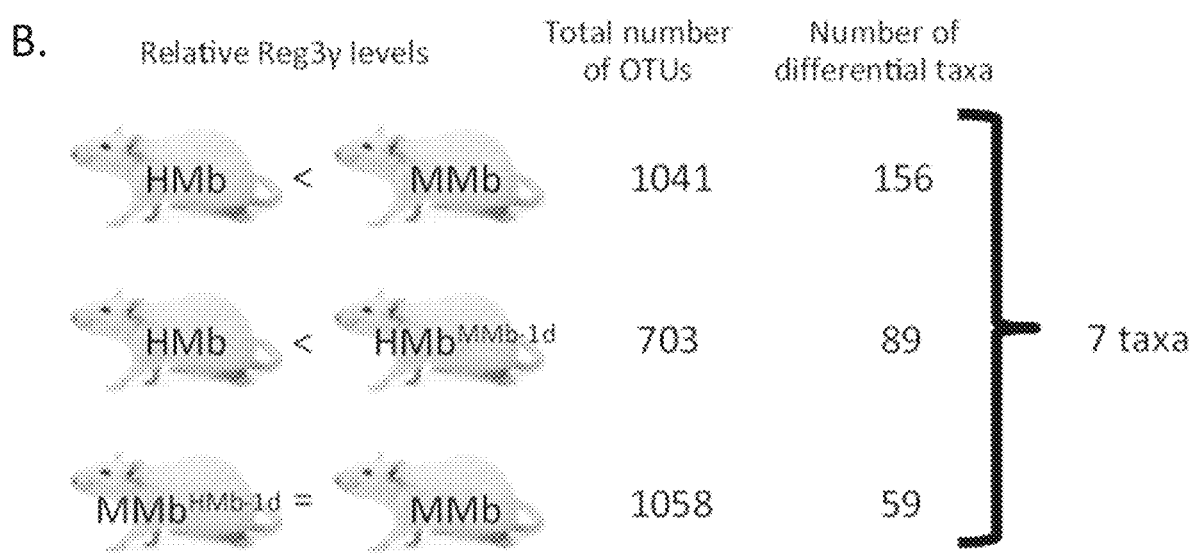

Figure 4
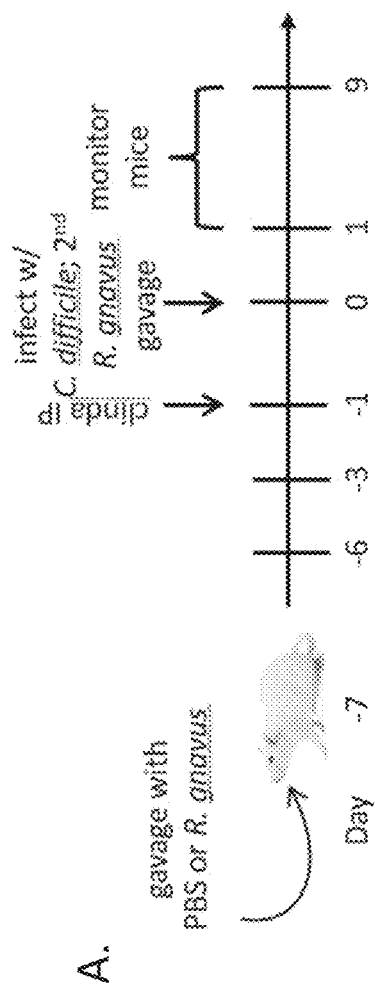
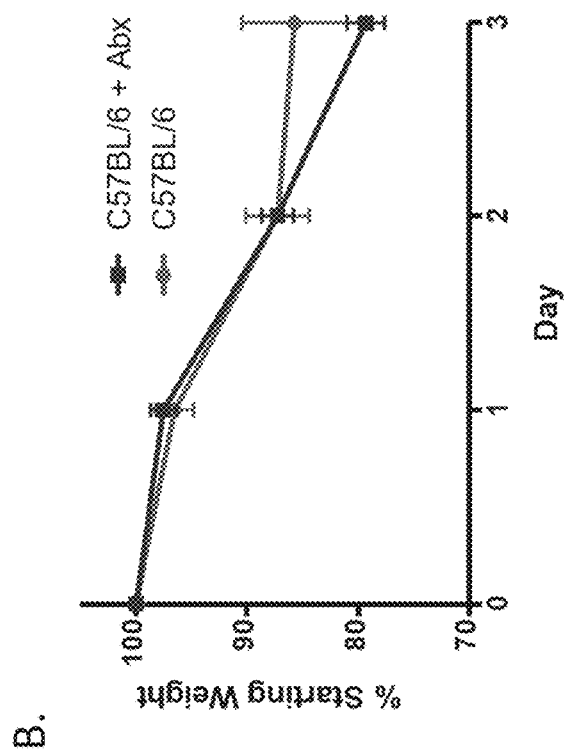

Figure 5
A.
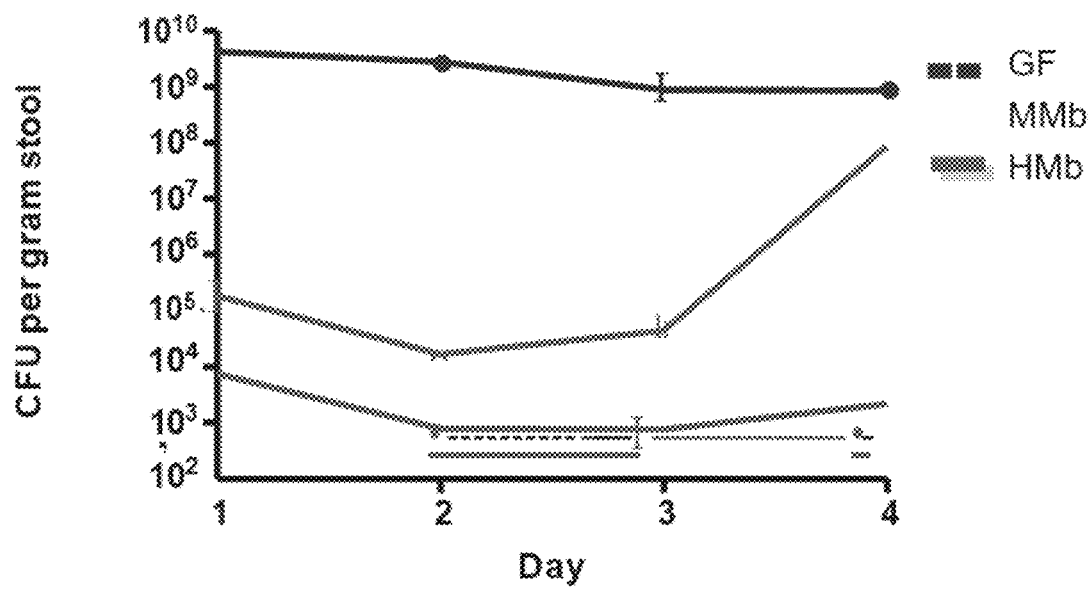
B.
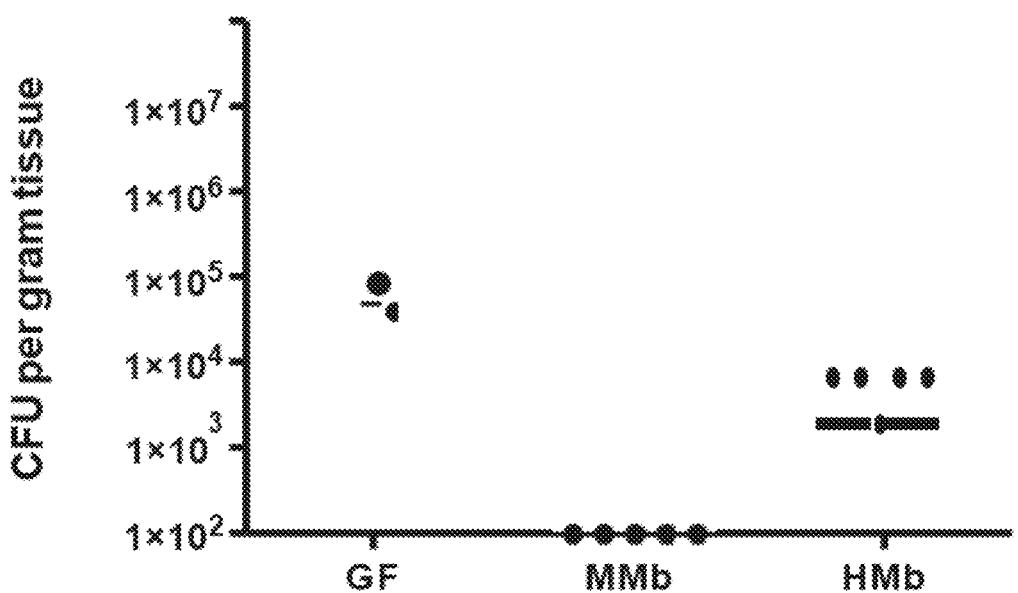

Figure 5 (continued)
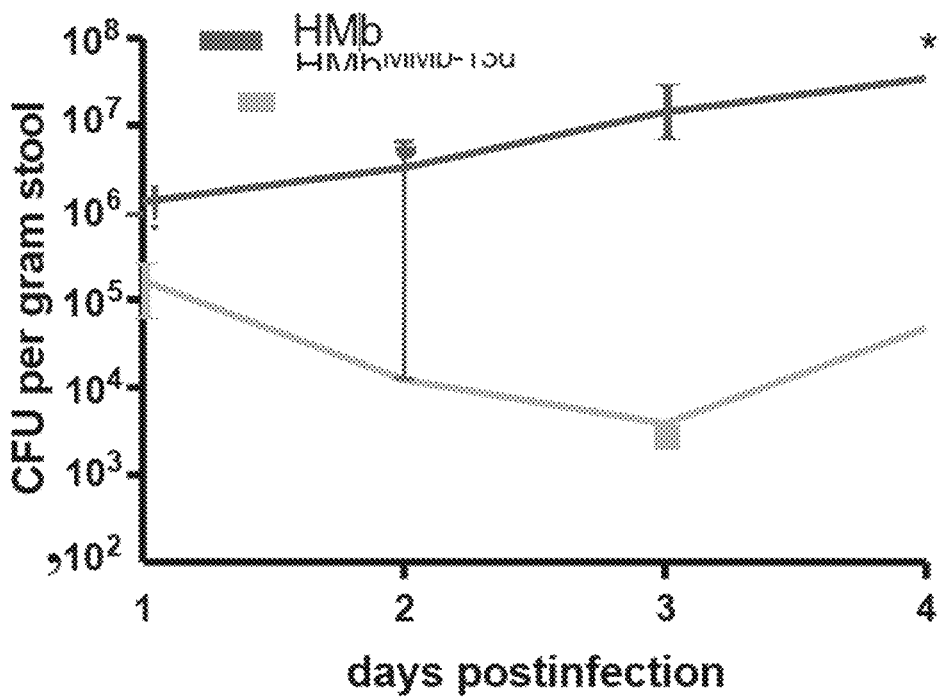
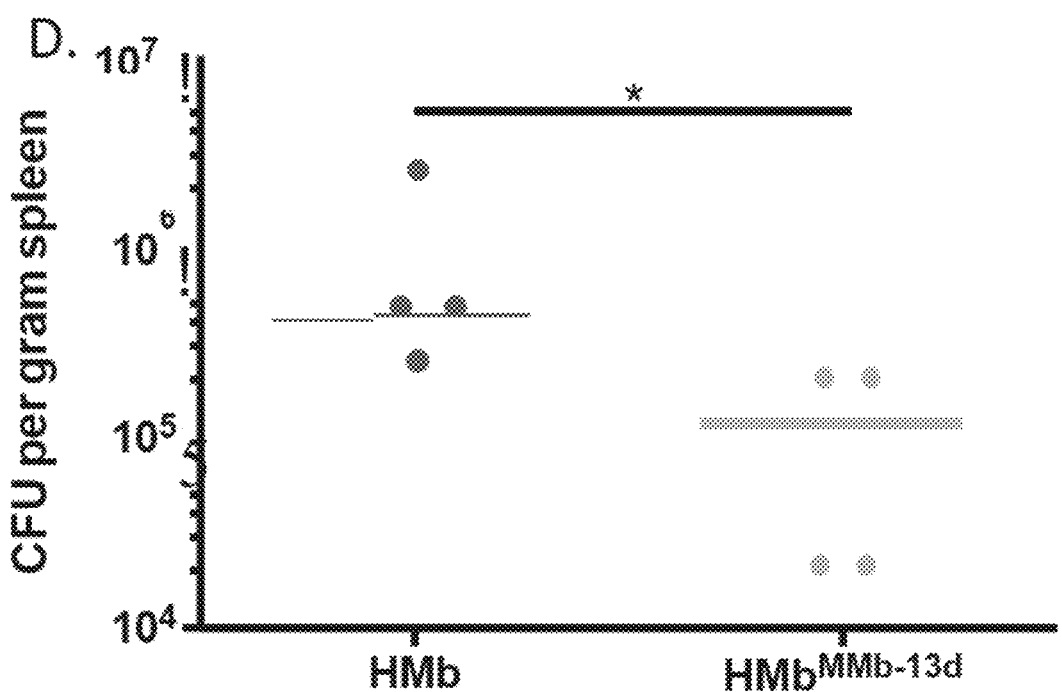

METHODS AND COMPOSITIONS TO TREAT AND PREVENT INFECTION

CROSS-REFERENCE TO RELATED APPLICATIONS

This application claims priority to U.S. Provisional Application No. 62/736,114 filed on Sep. 25, 2018, the contents of which are incorporated by reference in its entirety.

STATEMENT REGARDING FEDERALLY SPONSORED RESEARCH

This invention was made with Government support of Grant No. K08 AI108690 and U19 AI109764, awarded by the National Institutes of Health. The Government has certain rights in this invention.

BACKGROUND

The identification of penicillin in 1928 and its introduction into clinical medicine in the 1940s opened a "Golden Age" in medicine. Numerous antibiotics were discovered over the next several decades, leading to countless lives saved and the widespread idea in the 1960s that "the war against pestilence" had been won'. However, in this arms race between antibiotic-resistant bacteria and humans, the microbes have typically been more creative and adaptive. Clinically relevant resistance has developed rapidly after the introduction of new antibiotics, and antimicrobial-resistant organisms now account for >2 million infections, >23,000 deaths, and economic costs of >$50 billion dollars annually. Although investigators in academia and industry are fervently working on designing new antimicrobials, real progress in these endeavors has been slow. Moreover, history indicates that any success in the development of novel antibiotics will probably continue to be short-lived because of the rapid generation of resistance. Ultimately, a fundamentally different approach to the treatment of infections, particularly those involving antibiotic-resistant organisms, is sorely needed.

SUMMARY

In some aspects, provided herein are methods, beneficial bacteria, and compositions useful in treating and preventing bacterial infections by increasing the presence of antimicrobial peptides within the subject. In some aspects, provided herein are methods of treating or preventing bacterial infections in a subject in need thereof by administering R. gnavus to the subject. In some aspects, provided herein are methods of treating or preventing bacterial infections in a subject in need thereof by administering L. reuteri to the subject. In some aspects, provided herein are methods of treating or preventing bacterial infections in a subject in need thereof by administering a combination of R. gnavus and L. reuteri to a subject.

In some aspects, provided herein are methods of increasing the levels of a Reg3 peptide (e.g., Reg3α, Reg3γ, Reg 3β or combinations thereof) in a subject in need thereof, by administering to the subject R. gnavus.

In some aspects, provided herein are methods of increasing the levels of a Reg3 peptide (e.g., Reg3α, Reg3γ, Reg3β or combinations thereof) in a subject in need thereof, by administering to the subject L. reuteri.

In some aspects, provided herein are methods of increasing the level of a Reg3 peptide (e.g., Reg3α, Reg3γ, Reg3β and/or combinations thereof) in a subject in need thereof, by administering a combination of R. gnavus and L. reuteri.

In some aspects, the bacterial infection is a gram-positive bacterial infection. In some aspects, the bacterial infection is a gram-negative bacterial infection.

In some embodiments, the bacterial infection is an enterococci (e.g., vancomycin-resistant enterococci) infection, a C. difficile infection, or a Staphylococcus aureus (e.g., methicillin-resistant Staphylococcus aureus) infection. In some embodiments, the infection is caused by antibiotic-resistant bacteria. The R. gnavus and/or L. reuteri may be in a composition (e.g., a composition with a pharmaceutically acceptable carrier), and the composition may be formulated for oral administration. The composition may be a food product. The R. gnavus and/or L. reuteri may be in a composition with pharmaceutically acceptable carrier, and the composition may be formulated for rectal administration. The R. gnavus and/or L. reuteri may be in a composition with pharmaceutically acceptable carrier, and the composition may be formulated for topical or local administration. The compositions may comprise live, replication competent R. gnavus and/or L. reuteri. In some embodiments, the compositions do not comprise live, replication competent R. gnavus and/or L. reuteri. In some embodiments, the composition may be a bacterial lysate.

In another aspect, a method of increasing expression of cryptdin or human defensin 5 in a subject in need thereof is provided. The method comprises administering a composition comprising R. gnavus in an amount effective to increase the amount of cryptdin or human defensin 5 in the subject. In some aspects, the subject has a bacterial infection. In some aspects, the subject has a viral infection.

In another aspect, a method of increasing expression of lysozyme within a subject is provided. The method comprises administering an effective amount of R. gnavus in an amount effective to increase the expression of lysozyme in the subject.

In some aspects, provided herein are methods of treating or preventing bacterial infections in a subject in need thereof by administering R. gnavus, L. reuteri or combinations thereof to the subject in an amount effective to increase one or more antimicrobial peptides on order to reduce, inhibit or prevent the spread of the bacteria within the subject.

In another aspect, compositions comprising R. gnavus, L. reuteri or combinations thereof are provided. In some aspects, the compositions are formulated for systemic administration. In some aspects, the compositions are formulated for local administration.

Actual dosage levels of the bacteria in the compositions described herein may be varied so as to obtain an amount of the bacteria which is effective to achieve the desired therapeutic response for a particular patient. A physician or veterinarian having ordinary skill in the art can readily determine and prescribe the effective amount of the composition required.

BRIEF DESCRIPTION OF THE DRAWINGS

FIG. 4 shows *R. gnavus* protects SPF mice from *C. difficile* infection. A. Schematic of the experimental design. B. Weight loss in SPF C57BL/6J mice treated with antibiotics (gentamicin, metronidazole, colistin, and vancomycin) plus clindamycin or with clindamycin alone prior to *C. difficile* infection. C. Weight loss in SPF mice orally given *R. gnavus* before *C. difficile* challenge.

FIG. 5 shows that $HMb^{MMb-13d}$ mice have less severe *Salmonella* disease than HMb mice. Burden of *Salmonella* in feces on days 1-4 post-infection (A, C) and in the spleen on day 4 post-infection (B, D).

DETAILED DESCRIPTION

Definitions

For convenience, certain terms employed in the specification, examples, and appended claims are collected here.

The articles "a" and "an" are used herein to refer to one or to more than one (i.e., to at least one) of the grammatical object of the article.

As used herein, the term "administering" means providing an agent or composition to a subject, and includes, but is not limited to, administering by a medical professional and self-administering.

As used herein, the phrase "pharmaceutically-acceptable carrier" means a pharmaceutically-acceptable material, composition or vehicle, such as a liquid or solid filler, diluent, excipient, or solvent encapsulating material, involved in carrying or transporting an agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As used herein, the term "subject" means a human or non-human animal selected for treatment or therapy. The subjects may be humans or animals, for examples, livestock animals such as cattle, pigs, fowls, chickens, or companion animals such as horses, cats dogs, birds, and the like. In certain embodiments, of the methods and compositions described herein the subject is a human subject. In some embodiments, the subject suffers from or is prone to bacterial infections.

"Treating" a disease in a subject or "treating" a subject having a disease refers to subjecting the subject to a pharmaceutical treatment, e.g., the administration of a drug, such that at least one symptom of the disease is decreased or prevented from worsening. The term encompasses alleviation, reduction or prevention of one or more symptoms, slowing or stopping the progression or worsening of a disease, disorder, or condition, and/or the remission of the disease, disorder or condition.

Figure 7:
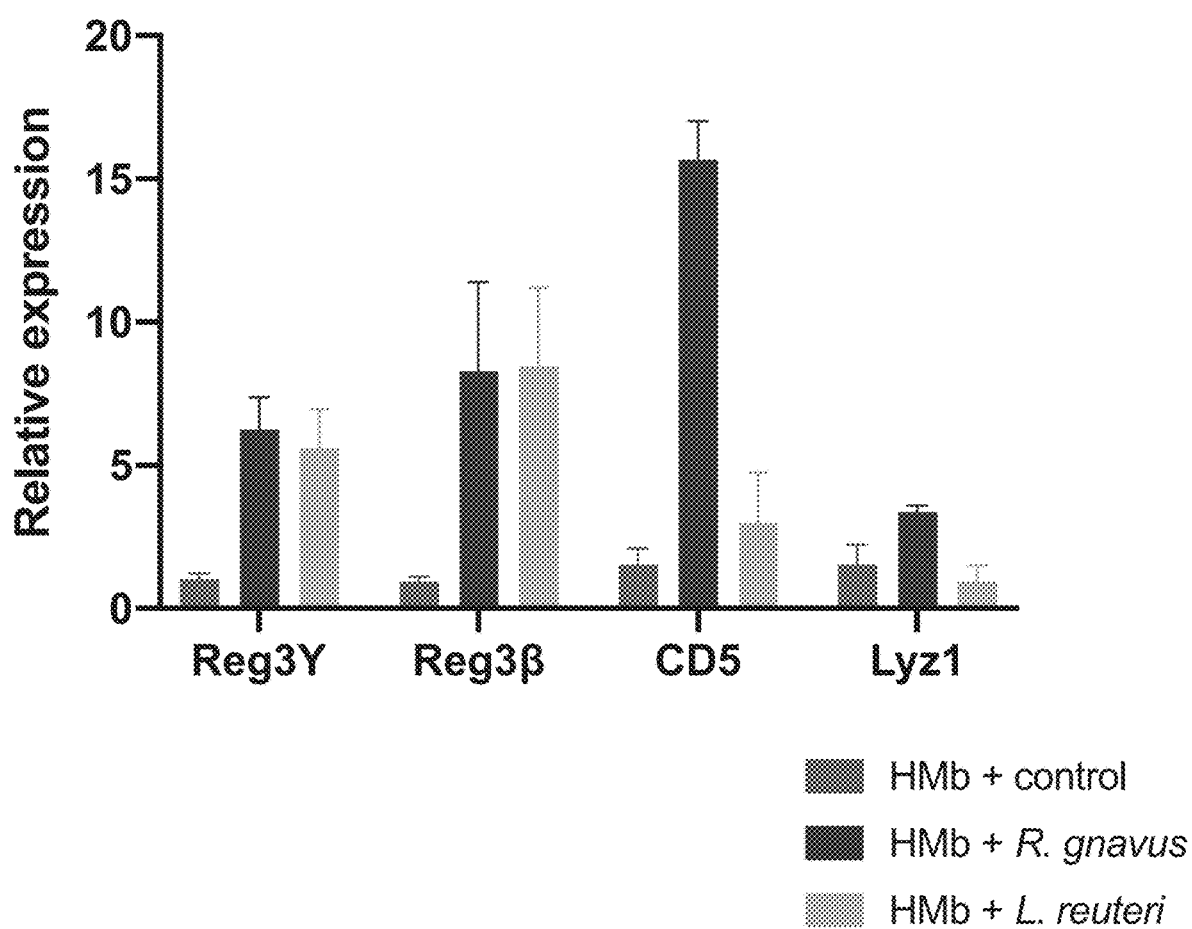
FIG. 7 shows *R. gnavus* and *L. reuteri* have different effects on Paneth cell antimicrobial peptides. qPCR analysis of Reg3γ, Reg3β, CD5 and Lyz1 expression on Paneth cells. *R. gnavus* induces a broad array of antimicrobial peptides, including Reg3g (primarily affects Gram-positive organisms), Reg3b (affects Gram-negative organisms), cryptdin 5 (a murine analog of human defensin 5, which has antibacterial activity along with antiviral activities, e.g., against adenovirus, HSV, influenza, HPV, HIV), and lysozyme (affects Gram-positive organisms). In contrast, *L. reuteri* more specifically induces Reg3g and Reg3b. These data are all from the ileum. Mice were gavaged once with the indicated bacteria (control: *P. distasonis*), sacrificed 7 days later, and ileal tissue was harvested for qPCR.

The present disclosure provides beneficial strains of bacteria, as in Table 1, for example, *R. gnavus* and *L. reuteri* are protective against colonization and infection with both gram negative and gram positive bacteria by increasing the expression of antimicrobial peptides, e.g., Reg3γ, Reg3β, Reg3α, cryptdin 5, defensing 5, lysozyme or combinations thereof within the subject, particularly within the gut (intestines) of the subject. As described in the examples below, the present invention demonstrates that *R. gnavus* and/or *L. reuteri* is able to provide protection from both gram negative (e.g., *Salmonella*) and gram positive (e.g., vancomycin-resistant enterococci (VRE), methicillin-resistant *Staphylococcus aureus* (MRSA) and *C. difficile*) infection by increasing the amount of anti-microbial peptides within the subject. *R. gnavus* also induces a broad array of antimicrobial peptides, including Reg3γ (primarily affects Gram-positive organisms), Reg3β (affects Gram-negative organisms), cryptdin 5 (a murine analog of human defensin 5), and lysozyme (affects Gram-positive organisms) as depicted in FIG. 7. *R. gnavus* is sufficient for induction of Paneth cell antimicrobial gene expression (FIG. 8). *L. reuteri* more specifically induces Reg3γ and Reg3β within a subject.

Cryptdin5/defensin 5 has both antibacterial and antiviral properties. Upregulation of cryptdin5/defensin 5 by treatment of a subject with the beneficial bacteria *R. gnavus* can provide protection against viral infection and/or reduced viral load and spread when upregulated in a subject.

The present disclosure provides a method of increasing the expression or levels of a Reg3 peptide in a subject in need thereof, comprising administering to the subject bacteria capable of increasing Reg3 levels, for example, strain *R. gnavus, L. reuteri* or a combination thereof, in an amount effective to increase the level of Reg3 peptide in the subject. Suitably, the Reg3 peptide is increased within the small or large intestine of the subject. The increased expression or level of the Reg3 can be from expression in Paneth cells within the small intestine of the subject. In some examples, the expression or level of Reg can be from epithelial cells within the subject, for example, in the lung, skin or large intestine, among others. In some examples, the Reg3 peptide is Reg3α, Reg3γ, Reg3β, or a combination thereof. For example, as demonstrated in the examples, the method may comprise administering an amount effective to increase Reg3γ, Reg3β, or combinations thereof within the small intestine of a subject. The expression of one or more of the antimicrobial peptides (e.g., Reg3α, Reg3γ, Reg3β, or a combination thereof) within the subject can decrease the ability of gram negative and/or gram-positive bacteria to colonize, infect, and/or grow in the subject. Further, the expression of Cryptdin5/defensin 5 may decrease the ability of viruses to infect, replicate and/or spread in the subject.

Suitable viruses abled to be treated by the current methods and compositions include, but are not limited to, for example, adenovirus, herpes simplex virus (HSV), influenza, human papilloma virus (HPV), human immunodeficiency virus (HIV), human BK virus, JC virus, among others.

2016, Cell Host & Microbe 19, 227-239, the contents of which are incorporated by reference). In a further example, the bacterium and compositions described herein may be used to treat obesity (see, e.g., Winder et al 2016, Cell Metabolism 23, p. 413-426).

In another example, the bacterium and compositions described herein can be used for the treatment of colitis. Colitis is a chronic digestive disease characterized by inflammation of the inner lining of the colon. Colitis may be caused by numerous factors, including, but not limited to, for example, infection, loss of blood supply in the colon, Inflammatory Bowel disease, and invasion of the colon wall with collagen or white blood cells. Increasing the levels of Reg3 in a subject can treat one or more symptoms of colitis (see, e.g., Darnaud et al. Gastroenterology, Vol. 154, Issue 4, March 2018, p. 1009-1023).

Suitable bacteria that are able to increase the levels of antimicrobial peptides (e.g., Reg3) within the subject include, but are not limited to, the bacteria in Table 1, including, for example, the bacteria *R. gnavus, L. reuteri*, or a combination thereof. Suitable known species of *R. gnavus* include, but are not limited to, for example, *R. gnavus* VPI C7-9 (ATCC #29149, which genomic nucleotide sequence is known NCBI GenBank #AAYG02000000 (whole genome shotgun sequencing project) also submitted international depositary under the Budapest Treaty as #_____), but the disclosure is not so limiting and includes other strains that are capable of expression the antimicrobial peptides within a subject. Suitable known *L. reuteri* strains that are capable of increasing anti-microbial peptides (e.g. Reg3) include can be determined, but are not limited to, for example, *L. reuteri* CF48-3A (BEI #HM-102, genomic nucleic acid sequence GenBank: ACHG0000000 also submitted international depositary under the Budapest Treaty as #_____). One skilled in the art would be able to identify, select and test species of the bacterial within these genus that is able to increase levels of Reg3, cryptdin5/defensin, or lysozyme within a subject by using the methods described in the Examples. Particularly, strains of *R. gnavus* and *L. reuteri* can be identified and tested for the ability to upregulate the Reg3, cryptdin5/defensin5 or lysozyme by known methods of one skilled in the art.

TABLE 1

| |
|---|
| p__Bacteroidetes.c__Bacteroidia.o__Bacteroidales.f__.g__.s |
| p__Bacteroidetes.c__Bacteroidia.o__Bacteroidales.f__.Rikenellaceae.g__.s__ |
| p__Firmicutes.c__Bacilli.o__Lactobacillales.f__.g__.s__ |
| p__Firmicutes.c__Bacilli.o__Lactobacillales.f__Lactobacillaceae.g__*Lactobacillus*.s__*reuteri* |
| p__Firmicutes.c__Bacilli.o__Lactobacillales.f__Streptococcaceae.g__*AStreptococcus*.s__ |
| p__Firmicutes.c__Clostridia.o__Clostridiales.f__Clostridiaceae.g__*CandidatusArthromitus*.s__ |
| p__Firmicutes.c__Clostridia.o__Clostridiales.f__Lachnospiraceae.g__*Ruminococcus*.s__*gnavus* | p, phylum; c, class; o, order; f, family; g, genus; s, species. Taxonomic levels that lack information (e.g., f__.g__.s__) did not match named taxa present in the Greengenes database.

In some embodiments, the increased expression or level of Reg3, particularly Reg3γ within the subject results in the increase in stem cell proliferation within the subject, particularly in some embodiments, stem cell proliferation within the intestines of the subject (e.g., small intestine). The ability to increase stem cell proliferation may aid in the treatment of numerous diseases, including, for example, alcohol liver disease.

In another example, the compositions may be used to treat alcoholic liver disease. Alcohol liver disease is exacerbated by the microbial composition of the intestines, and increasing intestinal REG3 can protect against alcoholic steatohepatitis and alcohol liver disease (See e.g., Wang et al.

In some embodiments, the subject in need of increased expression of Reg3 is a subject having an inflammatory condition or disease. An inflammatory disease refers to a disease or condition which is characterized by aberrant inflammation (e.g., an increased level of inflammation compared to a control such as a healthy person not suffering from the disease). Suitable inflammatory diseases that can be treated include, but are not limited to, for example, colitis, inflammatory bowel disease, asthma, autoimmune disease, auto-inflammatory disease, Celiac disease, Crohn's disease, ulcerative colitis, collagenous colitis, necrotizing enterocolitis irritable bowel syndrome, short bowel syndrome, stagnant loop syndrome, chronic persistent diarrhea, intractable diarrhea of infancy, Traveler's diarrhea, small intestinal disease, chronic prostatitis, psoriasis, among others.

In another embodiment, the subject in need of increased expression of Reg3 is a subject having a bacterial infection, for example, a gram-positive bacterial infection, gram-negative bacterial infection or a combination thereof.

In another embodiment, the disclosure provides a method of treating a gram positive bacterial infection in a subject, the method comprising, consisting of, or consisting essentially of administering to the subject a therapeutically effective amount of a composition comprising one or more bacteria capable of inducing Reg3 (e.g., Reg3γ or Reg3β) in the subject to treat the gram positive bacterial infection in the subject. In some examples, the bacteria is *R. gnavus, L. reuteri* or combination thereof. In some embodiments, the disclosure provides a method of reducing, inhibiting or preventing the growth and spread of a gram positive bacterial infection in a subject, the method comprising, consisting of, or consisting essentially of administering to the subject a therapeutically effective amount of a composition comprising one or more bacteria capable of inducing Reg3 in the subject in order to reduce, inhibit or prevent the growth or spread of the gram positive bacteria in the subject. In some embodiments, the gram-positive bacterial infection is an antibiotic resistant infection.

In another embodiment, the disclosure provides a method of treating a gram negative bacterial infection in a subject, the method comprising, consisting of, or consisting essentially of administering to the subject a therapeutically effective amount of a composition comprising one or more bacteria capable of inducing Reg3 (e.g. Reg3β) in the subject to treat the gram negative bacterial infection in the subject. In some examples, the bacteria is *R. gnavus, L. reuteri* or combination thereof. In some embodiments, the disclosure provides a method of reducing, inhibiting or preventing the growth and spread of a gram negative bacterial infection in a subject, the method comprising, consisting of, or consisting essentially of administering to the subject a therapeutically effective amount of a composition comprising one or more bacteria capable of inducing Reg3 in the subject in order to reduce, inhibit or prevent the growth or spread of the gram negative bacteria in the subject. In some embodiments, the gram-negative bacterial infection is an antibiotic resistant infection.

The term "gram positive bacteria" refer to those bacteria that give a positive result in the gram strain test due to the thick peptidoglycan layer in the bacterial cell wall. Suitable pathogenic gram-positive bacteria that can be treated by the beneficial bacteria described herein include, but are not limited to, for example, Enterococci, *Staphylococcus* including *Staphylococcus aureus, Streptococcus* including *S. pneumoniae, C. difficile, Listeria, Corynebacterium diphtheria*, among others. Gram-positive bacteria that are resistant to antibiotics are known in the art and include, but are not limited to, for example, vancomycin-resistant enterococci (VRE), methicillin-resistant *Staphylococcus aureus* (MRSA), *C. difficile*, among others.

The term "gram-negative bacteria" refer to those bacteria that lose the crystal violet stain (and take the color of the red counterstain) in Gram's method of staining, and characteristic of bacteria that have a cell wall composed of a thin layer of peptidoglycan. Suitable pathogenic gram negative bacteria that can be treated by the beneficial bacteria described herein include, but are not limited to, for example, *Pseudomonas aeruginosa, Neisseria gonorrhoeae, Chlamydia trachomatis, Yersinia pestis, Salmonella, Klebsiella pneumoniae, Legionella pneumophila, Escherichia coli,* *Proteus mirabilis, Enterobacter cloacae, Serratia marcescens, Helicobacter pylori, Salmonella enteritidis, Salmonella typhi, Shigella, Cyanobacteria, Neisseria meningitidis,* among others. In one example, the bacteria is *Salmonella.*

In some embodiments, the pathogenic gram-positive bacterial infection colonizes the intestine. In some embodiments, the pathogenic gram-positive bacteria causes an enteric infection.

The present disclosure provides compositions for increasing or upregulating at least one antimicrobial peptide in a subject. The composition comprise one or more bacteria capable of upregulating or increasing antimicrobial peptides, e.g., Reg3 in a subject. In one example, the composition comprises a *R. gnavus*. In another example, the composition comprises *L. reuteri*. In another example, the composition comprises a combination of *R. gnavus* and *L. reuteri*. The compositions can comprise a pharmaceutically acceptable carrier.

The inventors have surprisingly found that the beneficial bacteria that can upregulate Reg3, e.g. *R. gnavus, L. reuteri,* or combination thereof, do not need to be live or whole bacteria to provide the beneficial effects within a subject (e.g., protect against and reduce bacterial infections within a subject). Further, it was surprisingly found that the bacterial lysates from the bacterial described herein can also confer the beneficial effects, and thus live and/or whole (native) bacteria and bacterial replication is not necessary within the subject. In some examples, the composition comprises *R. gnavus, L. reuteri,* or combination thereof wherein the bacteria are inactive and unable to grow or replicate (e.g., heat inactivated bacteria). The term inactive refers to "non-viable" bacteria that are not able to replicate or grow (e.g., may be killed by methods known in the art). Suitable way to inactivate bacteria include heat inactivation, ionizing radiation (gamma rays or electron beam), standard sterilization methods such as moist or dry heat, sterilant gas or vapor (see, e.g., Shintani et al., Biocontrol Science, 16(3):85-94, 2011). Other methods of killing bacterial are by treatment with an exogenous agent.

In some examples, the composition comprises a lysate made from *R. gnavus, L. reuteri*, or combination thereof. Methods of producing bacterial lysates are known in the art, and include, but are not limited to, adding an agent that disrupts the bacterial cell wall. In suitable embodiments, 100% of the bacteria are inactivated in the compositions described herein.

The beneficial bacteria that increase expression of Reg3, include but are not limited to, e.g., *R. gnavus, L. reuteri,* or combination thereof, may be formulated for different routes of administration.

For example, the composition may be formulated for systemic administration. For example, the composition can be formulated for oral administration. For oral administration, the active ingredient may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents.

Other suitable forms of the composition may be in the form of a powder, a suspension, a tablet, suspension, a suppository, a cream, an oil, an ointment, an oil-in-water emulsion, a water-in-oil emulsion, an aqueous solution, among others.

In another example, the composition may be formulated for local administration. Suitable local administration sites include, but are not limited to, the skin, lungs, gut, rectum etc. In one example, the formulations may be formulated for rectal administration. Suitable rectal formulations are known in the art and include, but not limited to, creams, ointments, suppositories and the like.

The composition can be formulated for topical administration, e.g., administration to the skin. The term "topical administration," as used herein, refers to local administration of a component of a composition of the invention onto the surface of a skin or mucosal tissue of a subject. A topical administration emphasizes local effect, and substance is applied directly where its action is desired. Suitably, the composition includes the *R. gnavus, L. reuteri*, or combination thereof and a cream, lotion, ointment or salve capable of being administered to the skin of a subject. In some examples, the topical formulation comprises inactivated bacteria or bacterial lysates.

In another example, the composition may be formulated for inhalation (e.g., to contact the lungs). For inhalation, inactive bacteria or bacteria lysates would be preferable forms of the bacteria in order to not provide organisms to colonize the lung.

For example, for use in treating pneumonia, a composition comprising the bacteria described herein can be used as in inhalant to locally treat the lung infection or lung inflammation associated with a bacterial infection. Suitably, the compositions may be formulated into aerosols to be administered by inhalation. Aerosols of liquid particles comprising the composition may be produced by any suitable means, such as with a pressure-driven aerosol nebulizer or an ultrasonic nebulizer. See, e.g., U.S. Pat. No. 4,501,729, incorporated by reference in its entirety. Nebulizers are commercially available devices known in the art which transform solutions or suspensions of the active ingredient into a therapeutic aerosol mist either by means of acceleration of compressed gas, typically air or oxygen, through a narrow orifice or by means of ultrasonic agitation. Suitable compositions for use in nebulizers consist of the active ingredient in a liquid carrier, the active ingredient comprising up to 40% w/w of the composition, but in some embodiments, preferably less than 20% w/w. In some embodiments, the carrier is water (and most preferably sterile, pyrogen-free water) or a dilute aqueous alcoholic solution, preferably made isotonic but may be hypertonic to body fluids by the addition of, for example, sodium chloride. Optional additives include preservatives if the composition is not made sterile, for example, methyl hydroxybenzoate, antioxidants, volatile oils, buffering agents and surfactants.

Aerosols of solid particles comprising the bacterial compositions may likewise be produced with any solid particulate medication aerosol generator. Aerosol generators for administering solid particulate medicaments to a subject are known in the art, for example, generate a volume of aerosol containing a predetermined metered dose of a medicament at a rate suitable for human administration. For example, a solid particulate aerosol generator may be, but not limited to, an insufflator or a metered dose inhaler. Suitable compositions for administration by insufflation include finely comminuted powders which may be delivered by means of an insufflator or taken into the nasal cavity in the manner of a snuff. Dry powder inhalers are devices used to deliver drugs, especially proteins to the lungs. Some of the commercially available dry powder inhalers include Spinhaler (Fisons Pharmaceuticals, Rochester, NY) and Rotahaler (GSK, RTP, NC). The powder employed in the insufflator may consist either solely of the active ingredient or of a powder blend comprising the active ingredient, a suitable powder diluent, such as lactose, and an optional surfactant.

The pharmaceutical composition is preferably in unit dosage form. In such form the preparation is divided into unit doses containing appropriate quantities of the active component.

The terms "effective amount" or "therapeutically effective amount" refer to an amount sufficient to effect beneficial or desirable biological or clinical results. That result can be reducing, inhibiting or preventing the growth of a pathogenic bacteria, or reducing, inhibiting or preventing one symptom of the disease or condition, for example, reducing or inhibiting inflammation in some cases inflammation associated with a bacterial infection.

In some embodiments, kits for carrying out the methods described herein are provided. The kits provided may contain the necessary components with which to carry out one or more of the above-noted methods. In one embodiment, the kit comprises a composition comprising one or more bacteria able to increase Reg3 expression in a subject as described herein.

The present invention has been described in terms of one or more preferred embodiments, and it should be appreciated that many equivalents, alternatives, variations, and modifications, aside from those expressly stated, are possible and within the scope of the invention.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

The present invention has been described in terms of one or more preferred embodiments, and it should be appreciated that many equivalents, alternatives, variations, and modifications, aside from those expressly stated, are possible and within the scope of the invention.

The invention will be more fully understood upon consideration of the following non-limiting examples.

EXEMPLIFICATION

In thinking about alternative strategies for treating antibiotic-resistant infections, it is useful to consider that infectious diseases result when host defenses are overwhelmed by the pathogen burden. Historically, treatments have focused on limiting the pathogen burden, either by directly targeting the pathogen via antibiotics or by debriding infected material (e.g., draining an abscess). A complementary therapeutic approach involves augmenting the host immune response such that host defenses can better contain the pathogen[3,4]. Conceptually, this is the rationale for using vaccines to target high-priority pathogens in order to engender protective immunity on a broad population level[5,6]. This concept has also been successfully applied to patient populations that are at high risk for certain types of infections (e.g., treating chronic granulomatous disease with interferon gamma; performing bone marrow transplants in patients with severe combined immunodeficiency)[7,8]. If this type of immunomodulation can be done in a safe and cost-effective manner, it may be possible to extend this model to a broader population of patients who are specifically at risk for infection with antimicrobial-resistant organisms.

Example 1

The microbiota is a potent source of immunomodulatory molecules.

The human microbiota—made up of the trillions of bacteria, viruses, fungi, and archaea that colonize individuals and outnumber human cells by 10- to 100-fold—represents an incredibly complex ecosystem that is intricately intertwined with host physiology[9]. After eons of coevolution, these bacteria exist in a truly mutualistic relationship with host cells, aiding with metabolism of nutrients, driving proper development of the intestinal epithelium, outcompeting pathogenic bacteria for anatomic niches, and serving an indispensable role in the development and maintenance of the host immune system[10-12]. The gut microbiota has been shown to confer many benefits, but its dysregulation may also play a role in the pathogenesis of many diseases characterized by inflammation and aberrant immune responses, such as infections, inflammatory bowel disease, type 1 diabetes, asthma, multiple sclerosis, and rheumatoid arthritis[13-18].

These observations underscore the potential role of microorganisms, particularly those in the gut microbiota, in regulating human health and disease. Indeed, the concept that commensal organisms contribute to host physiology dates back to Pasteur[19]. Over the past few decades, abundant epidemiologic data have revealed an inverse correlation between exposure to bacteria and the incidence of autoimmune and/or atopic diseases[20-22]. This correlation led to the "hygiene hypothesis," which has evolved over the past two decades and suggests that changes in microbial exposure—in combination with genetic susceptibilities—lead to a collapse of the normally highly coordinated, homeostatic immune response[22,23]. Overall, these epidemiologic findings strongly suggest that bacterial exposure shapes the human microbiota, ultimately augmenting the host immune response. However, identifying specific commensal organisms that modulate disease phenotypes has proven challenging. This endeavor has been complicated by the fact that members of the microbiota exhibit complicated interdependencies with abundant functional redundancies[24-27]. These hurdles have led to the notion that communities of organisms—not specific microbes—matter most in determining disease susceptibility. However, it is not clear whether this idea is accurate or simply reflects the difficulties inherent in discovering individual disease-modifying commensals.

Exploiting the Microbiota as Therapy

Given the putative role of the microbiota in regulating human health and disease, interest has resurged in using probiotics as therapy for many infectious, inflammatory, and/or autoimmune conditions that include a dysbiotic microbiota. Microbiota-based therapeutics have the potential to be more "natural" than conventional drugs, more closely address the root cause of illness, and may serve as a "polypill" for multiple conditions that arise from the same microbial derangement. Unfortunately, most studies of probiotics have yielded mixed results[28-33], probably because of three factors: (1) lack of mechanistic understanding of how a given probiotic might influence disease pathogenesis; (2) differences in the bacterial strains tested; and (3) heterogeneity in underlying clinical indications. Although there is tremendous interest in finding disease-protective commensal organisms, much of the microbiome field has focused on identifying organisms that exacerbate disease[34,35]. More recently, researchers have taken a step backward from studying specific probiotics to assessing the efficacy of fecal microbiota transplantation (FMT) as a generic proof of concept that microbiota-based therapy can ameliorate disease. Indeed, ~90% of patients with medically recalcitrant, recurrent *Clostridium difficile* infection are cured after transfer of stool from a healthy donor[36,37]. While these FMT studies have demonstrated great promise, they are difficult to standardize across large populations (given variability among stool donors); moreover, FMT is fraught with safety concerns and has an unclear mechanism of action[37-39]. To alleviate some of these concerns, companies have been trying to standardize a cultivable component of stool that can be used instead; SER-109, which encapsulates a complex mixture of bacteria and was the most promising of these products, failed to demonstrate efficacy in a highly anticipated phase II trial 2 years ago[40]. Again, this failure likely relates to a lack of understanding of the underlying mechanism of action—from either the bacterial or the host perspective—that precludes the ability to select the patient population most likely to benefit. Overall, although microbiota-based therapeutics have great potential, the demonstration of clinical successes may be difficult without a better understanding of the molecular mechanisms underlying these microbe-host interactions.

Microbiota-induced expression of antibacterial peptides is a critical defense against infections.

It is clear that compositional differences in the microbiota contribute significantly to susceptibility to and the severity of infectious diseases[14,41-43]. A key microbiota-regulated innate defense mechanism is the expression of antimicrobial peptides, including the C-type lectins of the Reg3 family[44-46]. These proteins are expressed by Paneth cells in the small intestine and epithelial cells in the colon, localize to the inner mucus layer, and require trypsin-mediated cleavage of an N-terminal propeptide to activate antibacterial activity[44,47,48]. The Reg proteins bind to components of the cell envelope, form a pore in the bacterial membrane, and lyse the cell[44,49-52]. The best-studied of these molecules in the mouse is Reg3γ (human ortholog: Reg3α), which binds to bacterial peptidoglycan with a dissociation constant of 11 nM[44,49]. Reg3γ is directly bactericidal against gram-positive organisms in low micromolar concentrations but has little to no activity against gram-negative organisms[44,47]. Murine Reg3β (human ortholog: Reg3γ) similarly binds peptidoglycan and exhibits some activity against gram-positive organisms[49]; however, it also binds the lipid A portion of lipopolysaccharide, a feature that makes Reg3β bactericidal against many gram-negative organisms[45,50]. Given that infections due to antibiotic-resistant organisms often begin with mucosal colonization, particularly of the intestinal epithelium[53-56], these antimicrobial peptides form a critical component of the host's innate defenses against invading pathogens by creating a bacteriafree zone at the epithelial barrier[48,57]. These defenses are compromised in patients receiving broad-spectrum antibiotics as expression of the Reg3 family requires the microbiota[44,56,57]. Antibiotic treatment not only helps select for the emergence of antibiotic-resistant organisms but also simultaneously weakens natural host defenses against infections caused by these organisms. Accordingly, we hypothesize that restoration of Reg3 family expression—particularly in high-risk patients—will limit gastrointestinal colonization with antimicrobial-resistant organisms, thereby preventing and treating infections due to these organisms.

Discovery of *R. gnavus* and *L. reuteri* as potent inducers of Reg3γ expression.

The use of host-derived antimicrobial peptides as therapeutics complementary to conventional antibiotics has long been considered[3,58,59]. Unfortunately, these proteins cannot simply be used as therapeutics because of their short-half lives and their ability to target host cells when not regulated appropriately[58], and it has been unclear how best to induce their endogenous expression. Specific commensal organisms that can induce these antimicrobial peptides have been nearly impossible to identify given the immense challenges encountered in identifying causal microbes in standard microbiome-wide association studies. In a recently published comprehensive analysis of the immunomodulatory capacity of taxonomically diverse commensal microbes, none of 28 bacteria assessed for small-intestinal expression of Reg3γ caused significant induction—a finding that highlights the difficulties in identifying causal microbes[26].

Figure 1:
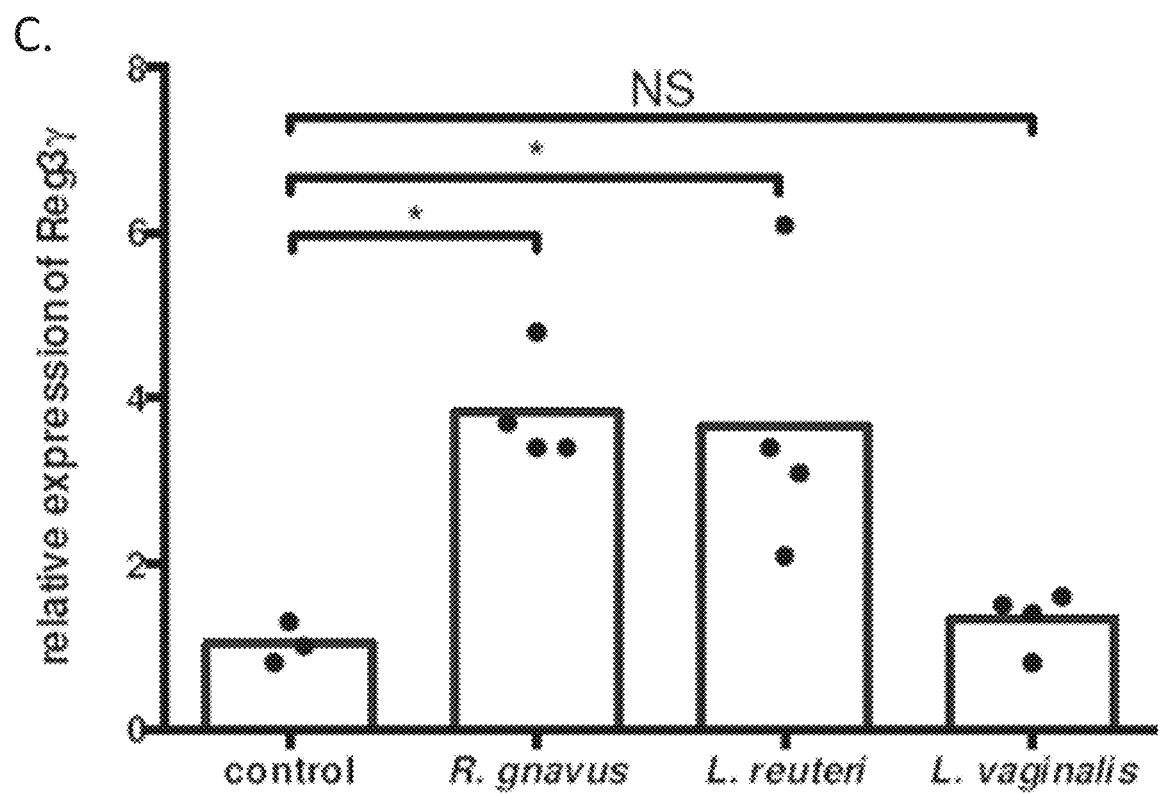
FIG. 1 shows R. gnavus and L. reuteri induce expression of Reg3γ (human ortholog Reg3α). A. qPCR analysis of Reg3γ expression in mice with varying microbiotas. B. The different pairwise comparisons used for triangulation; the total number of operational taxonomic units (OTUs) in each pair; and the number of differentially abundant taxa. C. qPCR analysis of Reg3γ expression in HMb mice after oral administration of the indicated bacteria. For all figures: NS, not significant; *, $p<0.05$; , $p<0.01$; *, $p<0.001$; ****, $p<0.0001$.

In work recently published in *Nature*, we developed an innovative platform that enables the efficient and highly specific identification of commensal organisms that are causally related to a phenotype of interest[60]. We previously showed that gnotobiotic mice harboring a normal human microbiota (HMb mice) have ileal levels of Reg3γ expression similar to those in germ-free (GF) mice and lower than those in gnotobiotic mice colonized with a mouse microbiota mice)[42]. Standard microbiome analyses identified more than 150 microbial taxa that were associated with this change in phenotype; this number is so large that it becomes extremely challenging to prioritize and pursue potential leads. Using an approach that has enjoyed some success in other microbiome studies, we identified two organisms that were present at appreciable levels in MMb mice and were completely absent from HMb mice; however, HMb mice treated with these organisms had no change in Reg3γ expression levels (data not shown). As an alternative approach, we reasoned that comparison of animals with more similar microbiotas should yield a shorter list of phenotype-associated microbial taxa and that cohousing of mice with different microbiotas should generate hybrid-microbiota animals reflective of both parental strains. If the microbial effect on disease were dominant, mapping of microbe-phenotype relationships in parental mouse strains and in hybrid-microbiota mice would enable us to triangulate disease-modulating organisms. Surprisingly, we found that cohousing of HMb and MMb mice for just 1 day restored Reg3γ expression levels in HMb mice exposed to MMb mice (HMb$^{MMb-1d}$) with no change seen in the cohousedMb mice (MMb$^{HMb-1d}$; FIG. 1A).

Ultimately, we identified differentially abundant bacteria in three different pairwise comparisons, including mouse pairs that were microbially related and mouse pairs in which the two animals varied in Reg3γ expression (FIG. 1B). We reasoned that if any taxa were truly relevant to disease pathogenesis, they would be differentially abundant in the two comparisons in which Reg3γ levels were different and would be the same in MMb and MMb$^{HMb-1d}$ mice in which Reg3γ levels were not different. When we applied this criterion, we refined the list of associated taxa from more than 150 to 7, 3 of which (*Ruminococcus gnavus*, *Lactobacillus reuteri*, and SFB) exhibit bioinformatic resolution to the species level. HMb mice treated once with *R. gnavus* or *L. reuteri* had increased levels of Reg3γ expression (FIG. 1C). The previous demonstration that SFB induce Reg3γ expression in GF and specific pathogen-free (SPF) mice confirms the more general applicability of results obtained in our specific gnotobiotic mice[8]. Importantly, our requirement that organisms be unchanged between MMb and MMb$^{HMb-1d}$ mice correctly excluded a relation between Reg3 expression and *Lactobacillus vaginalis*, a close relative of *L. reuteri* that is absent in HMb mice (FIG. 1C).

Microbe-phenotype triangulation is a robust platform for identifying causal microbes.

Figure 2:
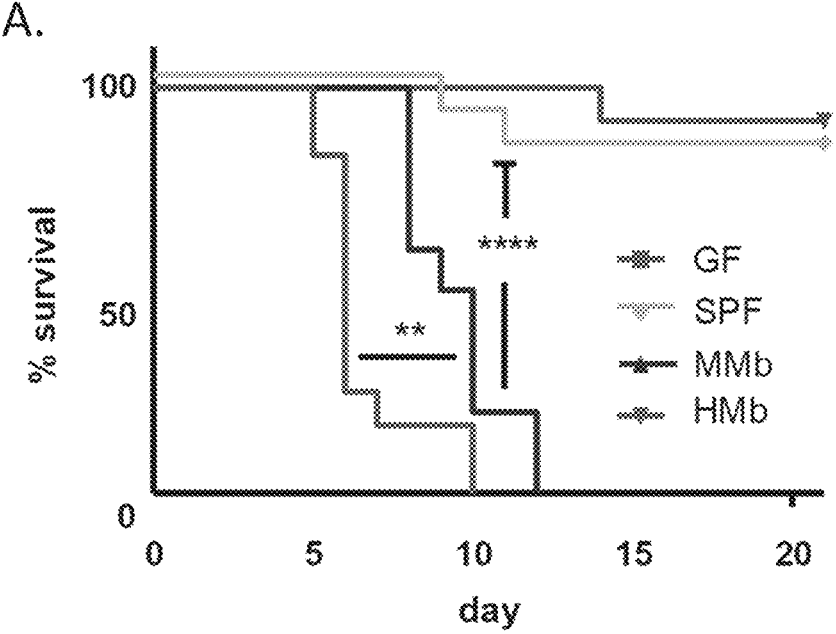
FIG. 2 shows that microbe-phenotype triangulation identifies *C. immunis* as protective against colitis. A. Survival curves of GF, MMb, HMb, and SPF mice after DSS challenge. B. The different pairwise comparisons used for triangulation; the total number of operational taxonomic units (OTUs) in each pair; the number of differentially abundant taxa; and the only taxon identified in all four comparisons. C. Survival of MMb mice orally receiving *C. innocuum* or *C. immunis* and subjected to DSS-induced colitis.
Figure 2:
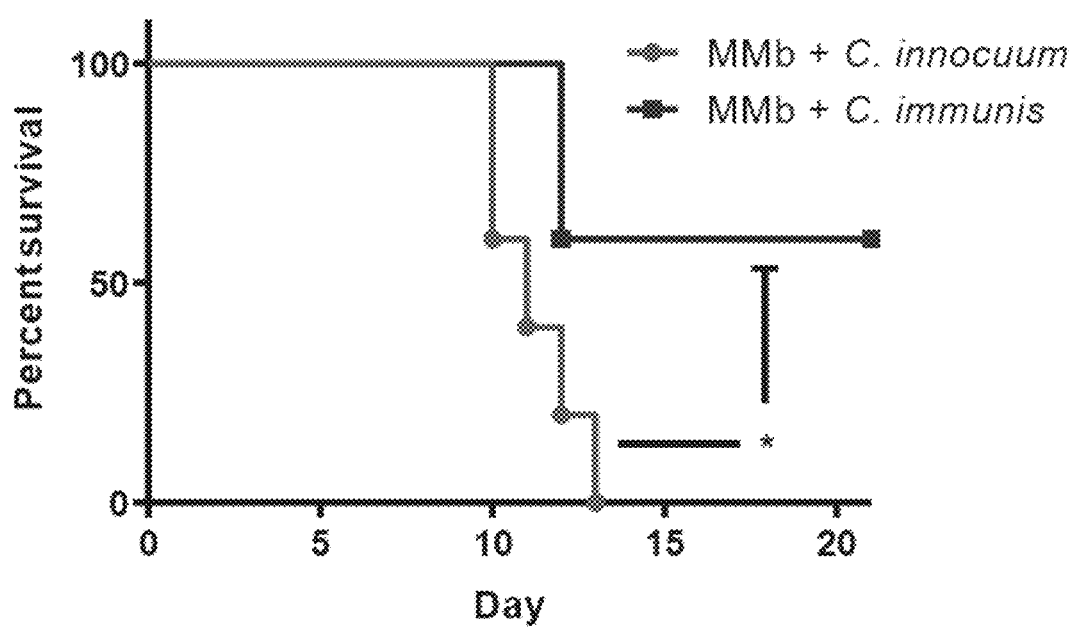

To demonstrate the generalizability of this platform, we also used microbe-phenotype triangulation to identify commensal bacteria that confer protection against colitis[60]. We demonstrated that HMb and HMb mice exhibited differential survival in the dextran sodium sulfate (DSS) colitis model (FIG. 2A). We again found that cohousing of MMb and HIVIb mice for 1 day resulted in altered phenotypes, with both MMb$^{HMb-1d}$ and MMb$^{HMb-1d}$ mice having intermediate phenotypes (data not shown). Using microbe-phenotype triangulation and the differentially abundant bacteria in four different pairwise comparisons, we identified a single taxon—the family Lachnospiraceae—that was the microbiologic correlate for protection from disease (FIG. 2B). Using directed microbial culture techniques, we isolated *Clostridium immunis*, a new bacterial species within Lachnospiraceae. Colitis-prone MMb mice orally treated with *C. immunis* were protected against colitis; in contrast, MMb mice treated with *Clostridium innocuum*, a non-Lachnospiraceae isolate also uniquely present in HMb mice, all succumbed to disease (FIG. 2C). Identification of taxonomically diverse microbes causally related to two disparate outcomes clearly demonstrates that our platform of microbe-phenotype triangulation represents a facile, straightforward approach for discovering key disease-modulating components of the microbiota. Moreover, in both examples, a single organism was sufficient to induce changes in the host, suggesting that the newfound ability to efficiently identify causal commensal organisms may hasten development of microbiota-based therapeutics. Along these lines, we are collaborating with industry to develop *C. immunis* as a live biotherapeutic product. This effort highlights the opportunity for developing other results born out of microbe-phenotype triangulation for clinical applications.

Example 2

Introduction

Since their inception, antibiotics have been the mainstay of treatment for infectious diseases; however, it is clear that newer, novel modalities are now needed to combat the growing threat of antimicrobial resistance[3,5,6]. There has recently been significant interest in harnessing intricate host-microbiome relationships as adjunctive therapy that can bolster endogenous defenses to help prevent and/or treat infections caused by antibiotic-resistant organisms[3,61]. However, two critical barriers have hampered the implementation of this approach: the difficulty in identifying specific commensal microbes with bona fide cause-effect relationships and a lack of understanding of the underlying mechanism(s) of action. Our innovative platform allowed for identification of causal microbes with a pathway-directed screen to effectively clear both of these hurdles, finally enabling the development of specific bacteria and bacterial factors as a new therapeutic modality for antibiotic-resistant infections. This approach may be useful for the treatment of acute infections by helping to contain the pathogen burden, but it is potentially most helpful in high-risk patient populations (e.g., patients receiving broad-spectrum antibiotics, patients known to be colonized with antibiotic-resistant organisms) in whom limiting colonization can prevent subsequent infection. This type of preventive approach has the added benefit of theoretically restraining the spread of antibiotic resistance by limiting the mingling of antibiotic-resistant organisms with antibiotic-sensitive organisms in the intestine—a hotbed of horizontal gene transfer. Although the field of microbiome research was initially full of hyperbolic hype, and although a few false starts assuaged previously unbridled optimism, investigators are now close to being able to treat the fundamental basis of many diseases, including antibiotic-resistant infections. The at least one bacterium described herein can be used for clinical use as anti-infectives.

Protective Nature of Reg3γ-Inducing Organisms

Reg3γ, the expression of which is regulated by commensal microbes, is a key regulator of host-microbe interactions[44,48]. Levels of Reg3γ expression directly correlate with colonization levels of antibacterial-resistant organisms—a critical precursor to invasive infection[56,57]. We have identified two taxonomically diverse organisms that are sufficient to induce Reg3γ expression. This Example demonstrates the therapeutic use of these Reg3 □-inducing organisms is protective against three of the most important gram-positive drug-resistant threats in a Reg3γ-dependent manner.

2A-Reg3γ-Inducing Organisms Provide Protection Against Gram Positive Pathogens (Vancomycin-Resistant Enterococci, MRSA, and *Clostridium difficile*)

Figure 3:
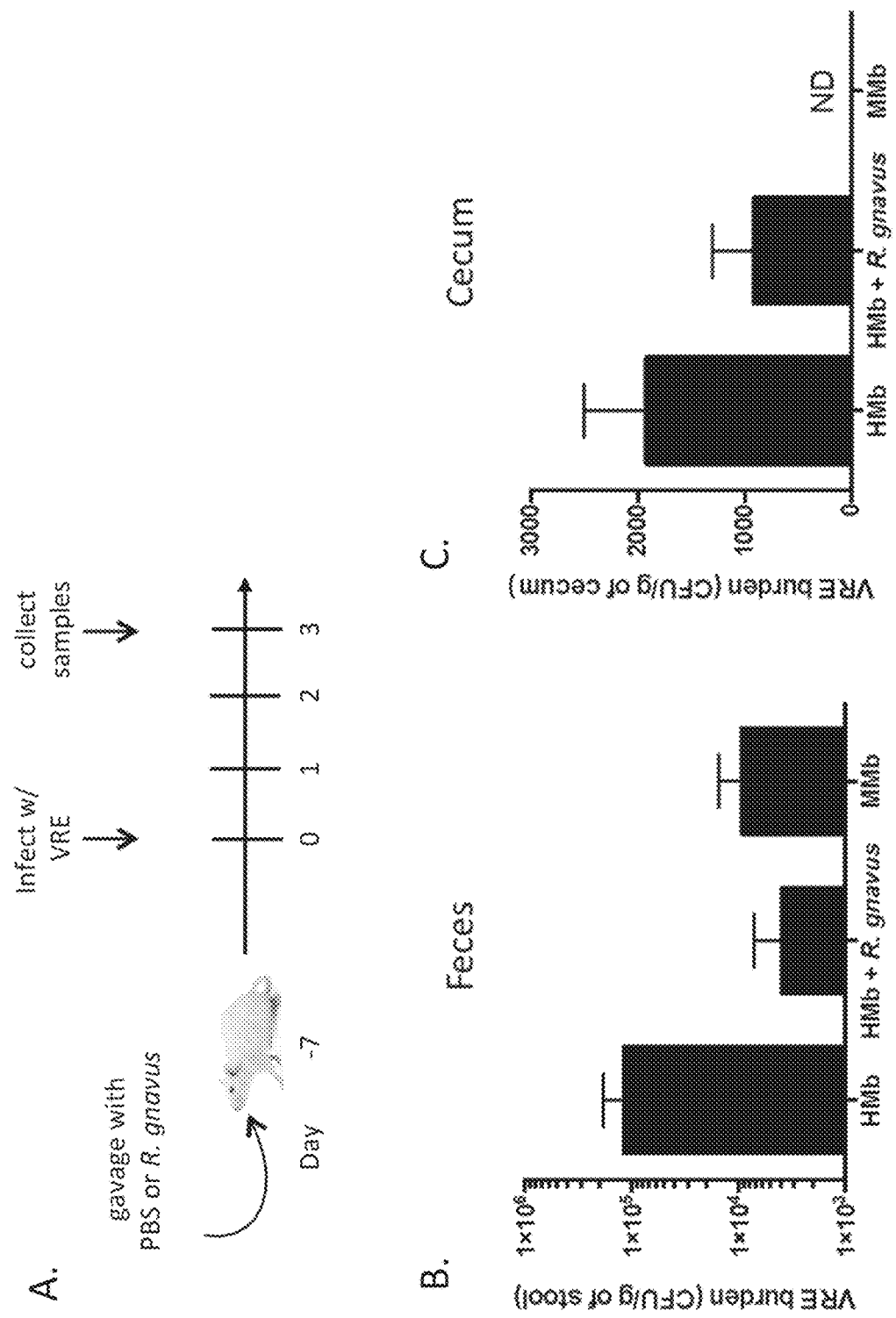
FIG. 3 shows *R. gnavus* protects HMb mice from VRE colonization. A. Schematic of the experimental design. B, C. Burden of VRE in feces (B) and adherent to the cecal epithelium (C) on day 3 post-infection.

Although Reg3γ is bactericidal against a wide range of gram-positive pathogens[44,57,62], its in vivo role has been best studied in the context of vancomycin-resistant enterococci (VRE), methicillin-resistant *Staphylococcus aureus* (MRSA), and *C. difficile*[56,57,62,63]. We demonstrate that Reg3γ induction by either *R. gnavus* or *L. reuteri* is protective against colonization and infection with these pathogens. In experiments exploring the relationship between the microbiota and susceptibility to VRE colonization, we found that MMb mice had a lower burden of VRE in the feces and adherent to the cecal epithelium on day 3 post-infection than did HMb mice (FIG. 3); this finding is consistent with protection against VRE by Reg3γ[57]. Importantly, results for HMb mice orally treated with *R. gnavus* 1 week prior to VRE challenge were similar to those for MMb mice (FIG. 3). These data shows that a single dose of *R. gnavus* can mediate protection against VRE.

We optimized the protocol for *C. difficile* infection to facilitate studies of the microbiota's effects. In murine models of *C. difficile* infection, mice are routinely pretreated with oral broad-spectrum antibiotics and then with a systemic dose of clindamycin 1 day prior to challenge (FIG. 4A). The broad-spectrum antibiotics transiently eliminate the microbiota, thereby complicating ascertainment of its effects (if there are any). We have found that mice treated only with a single dose of clindamycin prior to *C. difficile* infection still lose a significant amount of weight (FIG. 4B). Using this simpler model of *C. difficile* infection, we found that SPF C57BL/6J mice orally treated with two doses of *R. gnavus* lost far less weight after *C. difficile* infection than did control mice (FIG. 4C). These findings again illustrate the protective nature of *R. gnavus* against a clinically significant antibacterial-resistant pathogen.

The protective efficacy of *L. reuteri* will be tested as outlined in the general experimental design illustrated in FIG. 3A (for VRE and MRSA) and FIG. 4A (for *C. difficile*; treatment with clindamycin only). In all cases, we compare infections in SPF, MMb, and HMb mice as well as in SPF and HMb mice orally treated with either *L. reuteri* or *R. gnavus*. In each experiment, each group of mice will consist of ten 6- to 10-week-old animals. MMb mice will serve as a control for HMb mice, as we know that these two strains of gnotobiotic mice differ in Reg3γ expression; the inclusion of SPF mice will help determine whether *R. gnavus* and *L. reuteri* are effective in the setting of a normal microbiota and normal Reg3γ expression (as we observed with *C. difficile*). Mice will be infected with one of the following pathogens: VRE, ~$10^8$ colony-forming units (cfu) of strain HM-201 (BEI Resources); MRSA, ~$10^8$ cfu of a USA300 isolate (ATCC strain BAA-1717); or *C. difficile*, ~$10^5$ cfu of ATCC strain 43255. We will assess disease severity by monitoring weight loss and pathogen burden in feces and various intestinal segments (ileum, cecum, and colon).

In our preliminary experiments, mice received one or two doses of *R. gnavus* (~$10^7$ cfu per dose) prior to infection. This dosing schedule was of demonstrable benefit against VRE and *C. difficile*.

2—Protection Against Gram Positive and Gram Negative Bacteria and Viruses

Figure 8:
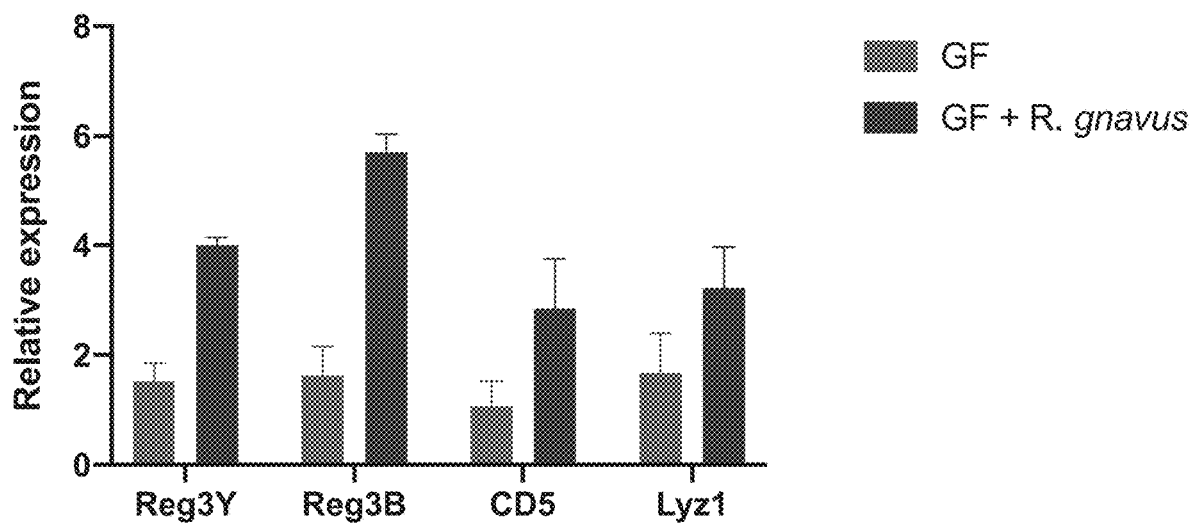
FIG. 8 demonstrates *R. gnavus* is sufficient for induction of Paneth cell antimicrobial gene expression. GF mice were gavaged with *R. gnavus*, sacrificed 7 days later, and the small intestine was harvested for qPCR analyses.

This Example demonstrates that *R. gnavus* and/or *L. reuteri* is able to provide protection from both gram negative (e.g., *Salmonella*) and gram positive (vancomycin-resistant enterococci (VRE), methicillin-resistant *Staphylococcus aureus* (MRSA) and *C. difficile*) infection. *R. gnavus* induces a broad array of antimicrobial peptides, including Reg3γ (primarily affects Gram-positive organisms), Reg3β (affects Gram-negative organisms), cryptdin 5 (a murine analog of human defensin 5, which has antibacterial activity along with antiviral activities, e.g., against adenovirus, HSV, influenza, HPV, HIV), and lysozyme (affects Gram-positive organisms) as depicted in FIG. 7. In contrast, *L. reuteri* more specifically induces Reg3γ and Reg3β. *R. gnavus* is sufficient for induction of Paneth cell antimicrobial gene expression (FIG. 8).

Figure 6:
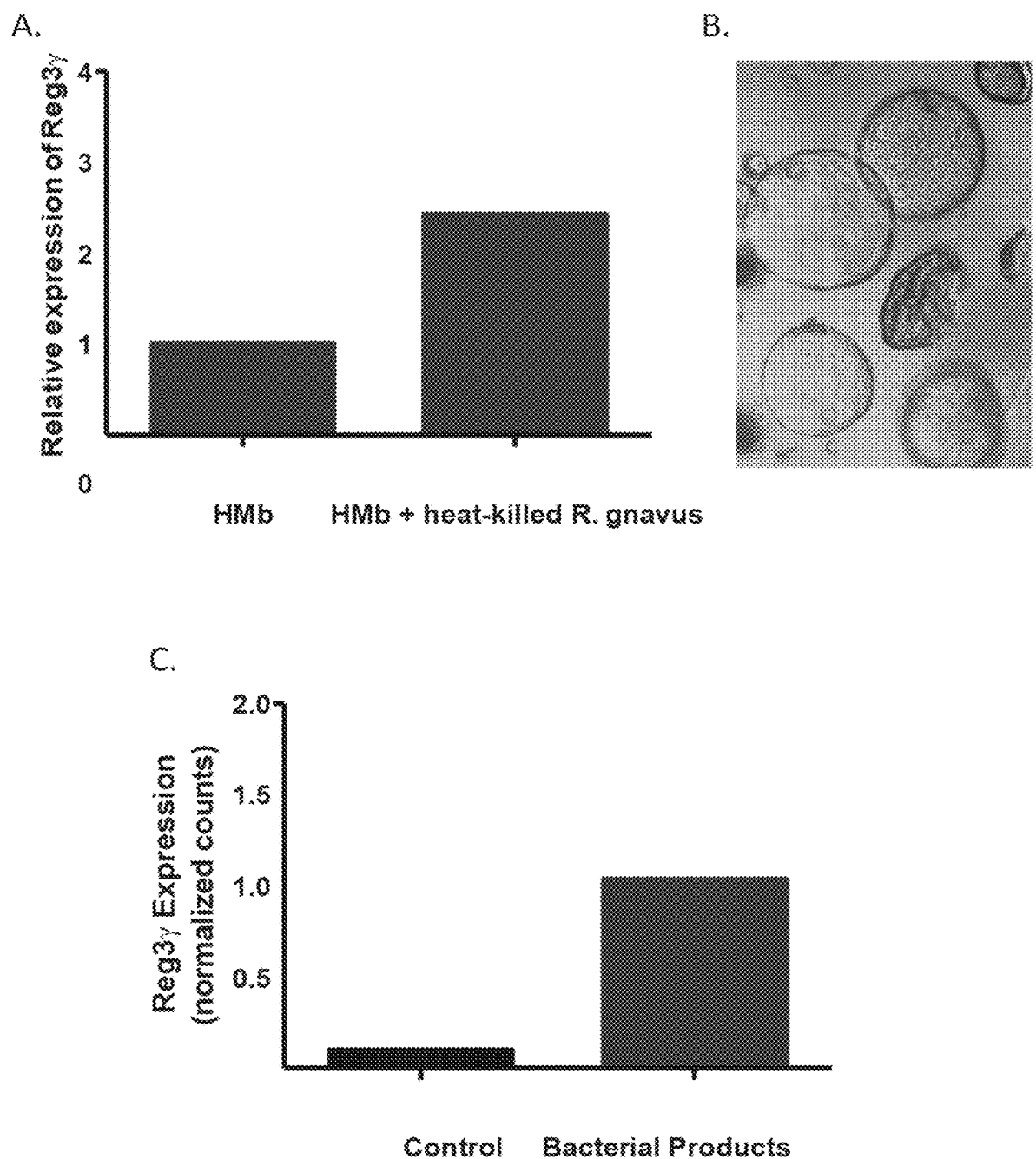
FIG. 6 shows bacterial products induce Reg3γ expression. A. qPCR analysis of Reg3γ expression. B. Photo of organoids before growth on Transwells. C. RNAseq analysis of Reg3γ expression in organoid-derived epithelial cells cultured with a crude mixture of bacterial products.
Figure 9:
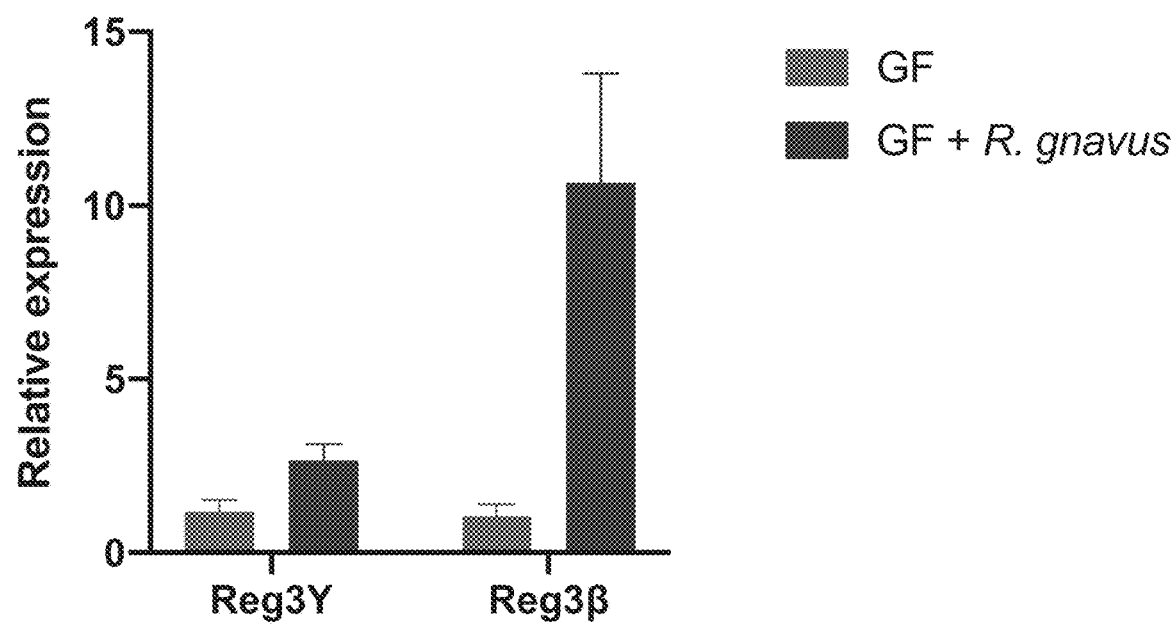
FIG. 9 demonstrates that *R. gnavus* also induces colonic Reg3γ and Reg 3β. GF mice were gavaged with *R. gnavus*, sacrificed 7 days later, and the colon was harvested for qPCR analyses.
Figure 10:
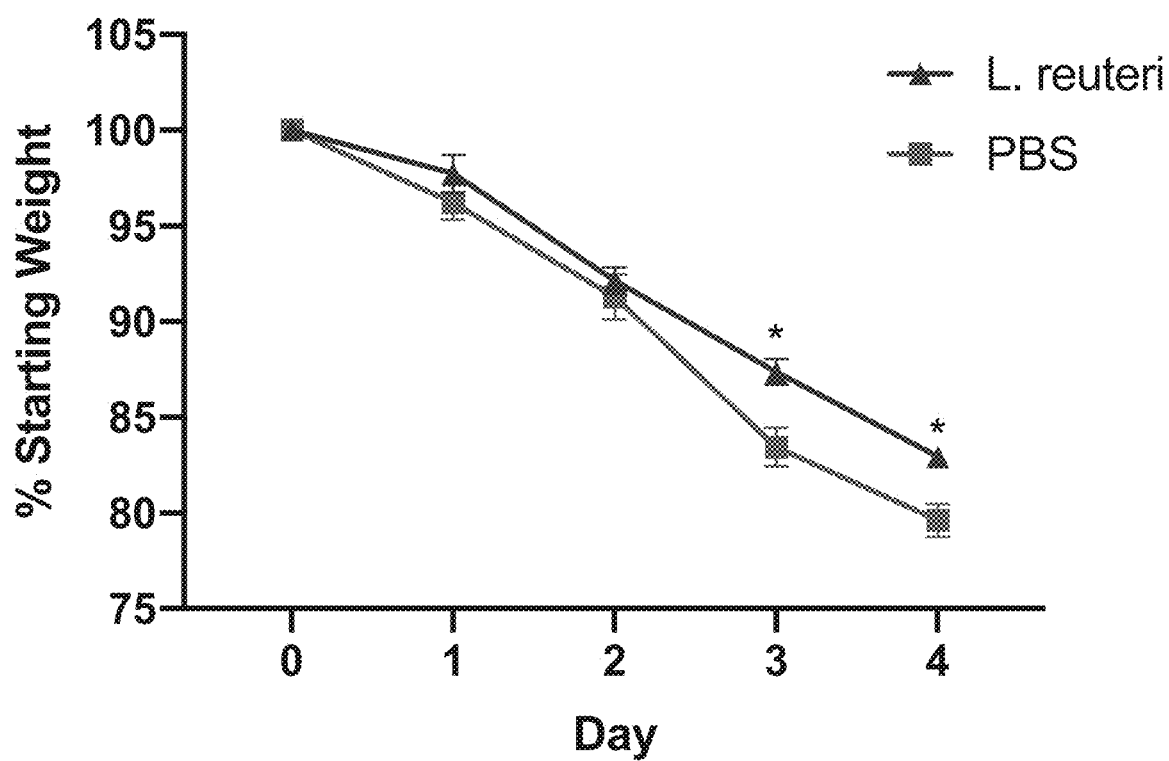
FIG. 10 shows *L. reuteri* protects HMb mice against *Salmonella*. HMb mice were treated with ~10^7 cfu *L. reuteri* 1 week prior to infection and on the same day as being infected with ~10^10 CFU *Salmonella*.

FIG. 6 demonstrates that bacteria do not need to be live to produce this protective effect and to induce antimicrobial peptide expression, as bacterial products can induce Reg3γ expression. *R. gnavus* also induces colonic Reg3γ and Reg 3β (FIG. 9), and *L. reuteri* protects HMb mice against *Salmonella* (gram-negative bacteria, FIG. 10).

FIG. 7 also demonstrates that *R. gnavus* has anti-viral capabilities, demonstrated by the increased expression of the cryptdin 5.

REFERENCES

1. Spellberg B, Guidos R, Gilbert D, et al. The epidemic of antibiotic-resistant infections: a call to action for the medical community from the Infectious Diseases Society of America. *Clin. Infect. Dis.* Jan. 15, 2008; 46(2):155-164.
2. CDC. Antibiotic resistance threats in the United States, 2013. Atlanta: CDC; 2013: www.cdc.gov/drugresistance/threat-report-2013/pdf/ar-threats-2013-508.pdf.

3. Czaplewski L, Bax R, Clokie M, et al. Alternatives to antibiotics-a pipeline portfolio review. *Lancet Infect. Dis.* February 2016; 16(2):239-251.
4. Hancock R E, Nijnik A, Philpott D J. Modulating immunity as a therapy for bacterial infections. *Nat. Rev. Microbiol.* Mar. 16, 2012; 10(4):243-254.
5. Jansen K U, Knirsch C, Anderson A S. The role of vaccines in preventing bacterial antimicrobial resistance. *Nat. Med.* Jan. 9, 2018; 24(1):10-19.
6. Rappuoli R, Bloom D E, Black S. Deploy vaccines to fight superbugs. *Nature.* Dec. 14, 2017; 552(7684):165-167.
7. Marciano B E, Wesley R, De Carlo E S, et al. Long-term interferon-gamma therapy for patients with chronic granulomatous disease. *Clin. Infect. Dis.* Sep. 1, 2004; 39(5):692-699.
8. Pai S Y, Logan B R, Griffith L M, et al. Transplantation outcomes for severe combined immunodeficiency, 2000-2009. *N Engl. J. Med.* Jul. 31, 2014; 371(5):434-446.
9. Surana N K, Kasper D L. Deciphering the tete-a-tete between the microbiota and the immune system. *J. Clin. Invest.* October 2014; 124(10):4197-4203.
10. Backhed F, Ley R E, Sonnenburg J L, Peterson D A, Gordon J I. Host-bacterial mutualism in the human intestine. *Science.* Mar. 25, 2005; 307(5717):1915-1920.
11. Hooper L V, Gordon J I. Commensal host-bacterial relationships in the gut. *Science.* May 11, 2001; 292 (5519):1115-1118.
12. Hooper L V, Wong M H, Thelin A, Hansson L, Falk P G, Gordon J I. Molecular analysis of commensal host-microbial relationships in the intestine. *Science.* Feb. 2, 2001; 291(5505):881-884.
13. Buffie C G, Bucci V, Stein R R, et al. Precision microbiome reconstitution restores bile acid mediated resistance to *Clostridium difficile. Nature.* Jan. 8, 2015; 517(7533):205-208.
14. Gauguet S, D'Ortona S, Ahnger-Pier K, et al. Intestinal microbiota of mice influences resistance to *Staphylococcus aureus* pneumonia. *Infect. Immun.* Jul. 27, 2015.
15. Round J L, Mazmanian S K. The gut microbiota shapes intestinal immune responses during health and disease. *Nat. Rev. Immunol.* May 2009; 9(5):313-323.
16. Sartor R B. Microbial influences in inflammatory bowel diseases. *Gastroenterology.* February 2008; 134(2):577-594.
17. Tlaskalova-Hogenova H, Stepankova R, Hudcovic T, et al. Commensal bacteria (normal microflora), mucosal immunity and chronic inflammatory and autoimmune diseases. *Immunol. Lett.* May 15, 2004; 93(2-3):97-108.
18. Wen L, Ley R E, Volchkov P Y, et al. Innate immunity and intestinal microbiota in the development of Type 1 diabetes. *Nature.* Oct. 23, 2008; 455(7216):1109-1113 Epub 28 Sep. 1121.
19. Schottelius M. Die Bedeutung der Darmbakterien far die Ernahrung. II. *Arch. Hyg. Bakteriol.* 1902; 42:48-70.
20. Bach J F. The effect of infections on susceptibility to autoimmune and allergic diseases. *N. Engl. J. Med.* Sep. 19, 2002; 347(12):911-920.
21. Ege M J, Mayer M, Normand A C, et al. Exposure to environmental microorganisms and childhood asthma. *N. Engl. J. Med.* Feb. 24, 2011; 364(8):701-709.
22. Strachan D P. Hay fever, hygiene, and household size. *BMJ.* Nov. 18, 1989; 299(6710): 1259-1260.
23. Ehlers S, Kaufmann S H. 99th Dahlem conference on infection, inflammation and chronic inflammatory disorders: lifestyle changes affecting the host-environment interface. *Clin. Exp. Immunol.* April 2010; 160(1): 10-14.
24. Atarashi K, Tanoue T, Oshima K, et al. Treg induction by a rationally selected mixture of Clostridia strains from the human microbiota. *Nature.* Aug. 8, 2013; 500(7461):232-236.
25. Faith J J, Ahern P P, Ridaura V K, Cheng J, Gordon J I. Identifying gut microbe-host phenotype relationships using combinatorial communities in gnotobiotic mice. *Sci. Transl. Med.* Jan. 22, 2014; 6(220):220ra211.
26. Geva-Zatorsky N, Sefik E, Kua L, et al. Mining the Human Gut Microbiota for Immunomodulatory Organisms. *Cell.* Feb. 23, 2017; 168(5):928-943 e911.
27. Rakoff-Nahoum S, Foster K R, Comstock L E. The evolution of cooperation within the gut microbiota. *Nature.* May 12, 2016; 533(7602):255-259.
28. Deshpande G, Rao S, Patole S, Bulsara M. Updated meta-analysis of probiotics for preventing necrotizing enterocolitis in preterm neonates. *Pediatrics.* May 2010; 125(5):921-930.
29. Kalliomaki M, Salminen S, Arvilommi H, Kero P, Koskinen P, Isolauri E. Probiotics in primary prevention of atopic disease: a randomised placebo-controlled trial. *Lancet.* Apr. 7, 2001; 357(9262):1076-1079.
30. Kligler B, Hanaway P, Cohrssen A. Probiotics in children. *Pediatr. Clin. North Am.* December 2007; 54(6): 949-967; xi.
31. Thomas D W, Greer F R. Probiotics and prebiotics in pediatrics. *Pediatrics.* December 2010; 126(6): 1217-1231.
32. Stapleton A E, Au-Yeung M, Hooton $T_M$, et al. Randomized, placebo-controlled phase 2 trial of a *Lactobacillus crispatus* probiotic given intravaginally for prevention of recurrent urinary tract infection. *Clin. Infect. Dis.* May 2011; 52(10):1212-1217.
33. Surawicz C M, Alexander J. Treatment of refractory and recurrent *Clostridium difficile* infection. *Nat. Rev. Gastroenterol. Hepatol.* June 2011; 8(6):330-339.
34. Palm N W, de Zoete M R, Cullen T W, et al. Immunoglobulin A coating identifies colitogenic bacteria in inflammatory bowel disease. *Cell.* Aug. 28, 2014; 158(5): 1000-1010.
35. Vatanen T, Kostic A D, d'Hennezel E, et al. Variation in Microbiome LPS Immunogenicity Contributes to Autoimmunity in Humans. *Cell.* May 5, 2016; 165(4):842-853.
36. Cammarota G, Ianiro G, Gasbarrini A. Fecal microbiota transplantation for thetreatment of *Clostridium difficile* infection: a systematic review. *J. Clin. Gastroenterol.* September 2014; 48(8):693-702.
37. van Nood E, Vrieze A, Nieuwdorp M, et al. Duodenal infusion of donor feces for recurrent *Clostridium difficile. N. Engl. J Med.* Jan. 31, 2013; 368(5):407-415.
38. Kelly C R, Kahn S, Kashyap P, et al. Update on Fecal Microbiota Transplantation 2015: Indications, Methodologies, Mechanisms, and Outlook. *Gastroenterology.* July 2015; 149(1):223-237.
39. Lee C H, Steiner T, Petrof E O, et al. Frozen vs Fresh Fecal Microbiota Transplantation and Clinical Resolution of Diarrhea in Patients With Recurrent *Clostridium difficile* Infection: A Randomized Clinical Trial. *JAMA.* January 122016; 315(2):142-149.
40. Martin J, Wilcox M. New and emerging therapies for *Clostridium difficile* infection. *Current opinion in infectious diseases.* December 2016; 29(6):546-554.
41. Bohnhoff M, Drake B L, Miller C P. Effect of streptomycin on susceptibility of intestinal tract to experimental Salmonella infection. *Proc. Soc. Exp. Biol. Med.* May 1954; 86(1):132-137.

42. Chung H, Pamp S J, Hill J A, et al. Gut immune maturation depends on colonization with a host-specific microbiota. *Cell*. Jun. 22, 2012; 149(7):1578-1593.
43. Honda K, Littman D R. The microbiome in infectious disease and inflammation. *Annu. Rev. Immunol.* 2012; 30:759-795.
44. Cash H L, Whitham C V, Behrendt C L, Hooper L V. Symbiotic bacteria direct expression of an intestinal bactericidal lectin. *Science*. Aug. 25, 2006; 313(5790):1126-1130.
45. Stelter C, Kappeli R, Konig C, et al. *Salmonella*-induced mucosal lectin RegIIIbeta kills competing gut microbiota. *PLoS One*. 2011; 6(6):e20749.
46. Vaishnava S, Behrendt C L, Ismail A S, Eckmann L, Hooper L V. Paneth cells directly sense gut commensals and maintain homeostasis at the intestinal host-microbial interface. *Proc. Natl. Acad. Sci. U.S.A*. Dec. 30, 2008; 105(52):20858-20863.
47. Mukherjee S, Partch C L, Lehotzky R E, et al. Regulation of C-type lectin antimicrobial activity by a flexible N-terminal prosegment. *J. Biol. Chem*. Feb. 20, 2009; 284(8):4881-4888.
48. Vaishnava S, Yamamoto M, Severson K M, et al. The antibacterial lectin RegIIIgamma promotes the spatial segregation of microbiota and host in the intestine. *Science*. Oct. 14, 2011; 334(6053):255-258.
49. Lehotzky R E, Partch C L, Mukherjee S, et al. Molecular basis for peptidoglycan recognition by a bactericidal lectin. *Proc. Natl. Acad. Sci. U.S.A*. Apr. 27, 2010; 107 (17): 7722-7727.
50. Miki T, Holst O, Hardt W D. The bactericidal activity of the C-type lectin RegMeta against Gram-negative bacteria involves binding to lipid A. *J. Biol. Chem*. Oct. 5, 2012; 287(41):34844-34855.
51. Mukherjee S, Zheng H, Derebe M G, et al. Antibacterial membrane attack by a pore-forming intestinal C-type lectin. *Nature*. Jan. 2, 2014; 505(7481):103-107.
52. van Ampting M T, Loonen L M, Schonewille A J, et al. Intestinally secreted C-type lectin Reg3b attenuates *salmonellosis* but not listeriosis in mice. *Infect. Immun*. March 2012; 80(3):1115-1120.
53. Acton D S, Plat-Sinnige M J, van Wamel W, de Groot N, van Belkum A. Intestinal carriage of *Staphylococcus aureus*: how does its frequency compare with that of nasal carriage and what is its clinical impact? *Eur. J. Clin. Microbiol. Infect. Dis*. February 2009; 28(2):115-127.
54. Boyce J M, Havill N L, Maria B. Frequency and possible infection control implications of gastrointestinal colonization with methicillin-resistant *Staphylococcus aureus*. *J. Clin. Microhiol*. December 2005; 43(12):5992-5995.
55. Misawa Y, Kelley K A, Wang X, et al. *Staphylococcus aureus* Colonization of the Mouse Gastrointestinal Tract Is Modulated by Wall Teichoic Acid, Capsule, and Surface Proteins. *PLoS Pathog*. July 2015; 11(7):e1005061.
56. Ubeda C, Taur Y, Jenq R R, et al. Vancomycin-resistant *Enterococcus* domination of intestinal microbiota is enabled by antibiotic treatment in mice and precedes bloodstream invasion in humans. *J. Clin. Invest*. December 2010; 120(12):4332-4341.
57. Brandl K, Plitas G, Mihu C N, et al. Vancomycin-resistant enterococci exploit antibiotic-induced innate immune deficits. *Nature*. Oct. 9, 2008; 455(7214):804-807.
58. Mukherjee S, Hooper L V. Antimicrobial defense of the intestine. *Immunity*. Jan. 20, 2015; 42(1):28-39.
59. Peters B M, Shirtliff M E, Jabra-Rizk M A. Antimicrobial peptides: primeval molecules or future drugs? *PLoS Pathog*. Oct. 28, 2010; 6(10):e1001067.
60. Surana N K, Kasper D L. Moving beyond microbiome-wide associations to causal microbe identification. *Nature*. Dec. 14, 2017; 552(7684):244-247.
61. Ouwehand A C, Forssten S, Hibberd A A, Lyra A, Stahl B. Probiotic approach to prevent antibiotic resistance. *Ann. Med*. 2016; 48(4):246-255.
62. Choi S M, McAleer J P, Zheng M, et al. Innate Stat3-mediated induction of the antimicrobial protein Reg3gamma is required for host defense against MRSA pneumonia. *J. Exp. Med*. Mar. 11, 2013; 210(3):551-561.
63. Sadighi Akha A A, Theriot C M, Erb-Downward J R, et al. Acute infection of mice with *Clostridium difficile* leads to eIF2alpha phosphorylation and pro-survival signalling as part of the mucosal inflammatory response. *Immunology*. September 2013; 140(1):111-122.
64. Bezkorovainy A. Probiotics: determinants of survival and growth in the gut. *Am. J. Clin. Nutr*. February 2001; 73(2 Suppl):399S-405S.
65. Moayyedi P. Fecal transplantation: any real hope for inflammatory bowel disease? *Current opinion in gastroenterology*. July 2016; 32(4):282-286.
66. Rossen N G, Fuentes S, van der Spek M J, et al. Findings From a Randomized Controlled Trial of Fecal Transplantation for Patients With Ulcerative Colitis. *Gastroenterology*. July 2015; 149(1): 110-118 e114.
67. Wang L, Fouts D E, Starkel P, et al. Intestinal REG3 Lectins Protect against Alcoholic Steatohepatitis by Reducing Mucosa-Associated Microbiota and Preventing Bacterial Translocation. *Cell Host Microbe*. Feb. 10, 2016; 19 (2): 227-239.
68. Islam D, Bandholtz L, Nilsson J, et al. Downregulation of bactericidal peptides in enteric infections: a novel immune escape mechanism with bacterial DNA as a potential regulator. *Nat. Med*. February 2001; 7(2): 180-185.
69. Peschel A, Otto M, Jack R W, Kalbacher H, Jung G, Gotz F. Inactivation of the dlt operon in *Staphylococcus aureus* confers sensitivity to defensins, protegrins, and other antimicrobial peptides. *J. Biol. Chem*. Mar. 26, 1999; 274(13):8405-8410.
70. Robey M, O'Connell W, Cianciotto N P. Identification of *Legionella pneumophila* rcp, a pagP-like gene that confers resistance to cationic antimicrobial peptides and promotes intracellular infection. Infect. Immun. July 2001; 69(7):4276-4286.
71. Sieprawska-Lupa M, Mydel P, Krawczyk K, et al. Degradation of human antimicrobial peptide LL-37 by *Staphylococcus aureus*-derived proteinases. *Antimicrob. Agents Chemother*. December 2004; 48(12):4673-4679.
72. Santiago M, Matano L M, Moussa S H, Gilmore M S, Walker S, Meredith T C. A new platform for ultra-high density *Staphylococcus aureus* transposon libraries. *BMC genomics*. Mar. 29, 2015; 16:252.
73. DeFrancesco A S, Masloboeva N, Syed A K, et al. Genome-wide screen for genes involved in eDNA release during biofilm formation by *Staphylococcus aureus*. *Proc. Natl. Acad. Sci. U.S.A*. Jul. 18, 2017; 114(29):E5969-E5978.
74. Rajagopal M, Martin M J, Santiago M, et al. Multidrug Intrinsic Resistance Factors in *Staphylococcus aureus* Identified by Profiling Fitness within High-Diversity Transposon Libraries. *mBio*. Aug. 16, 2016; 7(4).
75. Santa Maria J P, Jr., Sadaka A, Moussa S H, et al. Compound-gene interaction mapping reveals distinct roles for *Staphylococcus aureus* teichoic acids. *Proc. Natl. Acad. Sci. U.S.A.* Aug. 26, 2014; 111(34):12510-12515.

76. Valentino M D, Foulston L, Sadaka A, et al. Genes contributing to *Staphylococcus aureus* fitness in abscess- and infection-related ecologies. *mBio.* Sep. 2, 2014; 5(5): e01729-01714.

77. Pang T, Wang X, Lim H C, Bernhardt T G, Rudner D Z. The nucleoid occlusion factor Noc controls DNA replication initiation in *Staphylococcus aureus*. *PLoS Genet.* July 2017; 13(7):e1006908.

78. Larsson E, Tremaroli V, Lee Y S, et al. Analysis of gut microbial regulation of host gene expression along the length of the gut and regulation of gut microbial ecology through MyD88. *Gut.* August 2012; 61(8):1124-1131.

79. Reikvam D H, Erofeev A, Sandvik A, et al. Depletion of murine intestinal microbiota: effects on gut mucosa and epithelial gene expression. *PLoS One.* Mar. 21, 2011; 6(3):e17996.

80. Caporaso J G, Lauber C L, Walters W A, et al. Ultra-high-throughput microbial community analysis on the Illumina HiSeq and MiSeq platforms. *The ISME journal.* August 2012; 6(8):1621-1624.

81. McDonald D, Price M N, Goodrich J, et al. An improved Greengenes taxonomy with explicit ranks for ecological and evolutionary analyses of bacteria and archaea. *The ISME journal.* March 2012; 6(3):610-618.

82. Segata N, Izard J, Waldron L, et al. Metagenomic biomarker discovery and explanation. *Genome biology.* 2011; 12(6):R60.

83. Goodman A L, Kallstrom G, Faith J J, et al. From the Cover: Extensive personal human gut microbiota culture collections characterized and manipulated in gnotobiotic mice. *Proc. Natl. Acad. Sci. U.S.A.* Apr. 12, 2011; 108 (15):6252-6257.

84. Lagier J C, Hugon P, Khelaifia S, Fournier P E, La Scola B, Raoult D. The rebirth of culture in microbiology through the example of culturomics to study human gut microbiota. *Clin. Microbiol. Rev.* January 2015; 28(1): 237-264.

85. Caballero S, Carter R, Ke X, et al. Distinct but Spatially Overlapping Intestinal Niches for Vancomycin-Resistant *Enterococcus faecium* and Carbapenem-Resistant *Klebsiella pneumoniae*. *PLoS Pathog.* September 2015; 11(9): e1005132.

86. Pier G B, Meluleni G, Neuger E. A murine model of chronic mucosal colonization by *Pseudomonas aeruginosa*. *Infect. Immun.* November 1992; 60(11):4768-4776.

87. Blot S, Depuydt P, Vogelaers D, et al. Colonization status and appropriate antibiotic therapy for nosocomial bacteremia caused by antibiotic-resistant gram-negative bacteria in an intensive care unit. *Infect. Control Hosp. Epidemiol.* June 2005; 26(6):575-579.

88. Donskey C J. The role of the intestinal tract as a reservoir and source for transmission of nosocomial pathogens. *Clin. Infect. Dis.* Jul. 15, 2004; 39(2):219-226.

89. Skurnik D, Roux D, Aschard H, et al. A comprehensive analysis of in vitro and in vivo genetic fitness of *Pseudomonas aeruginosa* using high-throughput sequencing of transposon libraries. *PLoS Pathog.* 2013; 9(9):e1003582.

90. Skurnik D, Roux D, Cattoir V, et al. Enhanced in vivo fitness of carbapenem-resistant oprD mutants of *Pseudomonas aeruginosa* revealed through high-throughput sequencing. *Proc. Natl. Acad. Sci. U.S.A* Dec. 17, 2013; 110(51):20747-20752.

91. Kulasekara H D, Ventre I, Kulasekara B R, Lazdunski A, Filloux A, Lory S. A novel two-component system controls the expression of *Pseudomonas aeruginosa* fimbrial cup genes. *Mol. Microbiol.* January 2005; 55(2):368-380.

92. Basso P, Ragno M, Elsen S, et al. *Pseudomonas aeruginosa* Pore-Forming Exolysin and Type IV Pili Cooperate To Induce Host Cell Lysis. *mBio.* Jan. 24, 2017; 8(1).

93. Roux D, Danilchanka O, Guillard T, et al. Fitness cost of antibiotic susceptibility during bacterial infection. *Sci. Transl. Med.* Jul. 22, 2015; 7(297):297ra114.

94. Fumeaux C, Bernhardt T G. Identification of MupP as a New Peptidoglycan Recycling Factor and Antibiotic Resistance Determinant in *Pseudomonas aeruginosa*. *mBio.* Mar. 28, 2017; 8(2).

95. Greene N G, Fumeaux C, Bernhardt T G. Conserved mechanism of cell-wall synthase regulation revealed by the identification of a new PBP activator in *Pseudomonas aeruginosa*. *Proc. Natl. Acad. Sci. U.S.A.* Mar. 5, 2018.

96. Linehan J L, Harrison O J, Han S J, et al. Non-classical Immunity Controls Microbiota Impact on Skin Immunity and Tissue Repair. *Cell.* Feb. 8, 2018; 172(4):784-796 e718.

97. Ridaura V K, Bouladoux N, Claesen J, et al. Contextual control of skin immunity and inflammation by *Corynebacterium*. *J. Exp. Med.* Jan. 30, 2018.

98. Steed A L, Christophi GP, Kaiko G E, et al. The microbial metabolite desaminotyrosine protects from influenza through type I interferon. *Science.* Aug. 4, 2017; 357(6350):498-502.

99. Chin C S, Alexander D H, Marks P, et al. Nonhybrid, finished microbial genome assemblies from long-read SMRT sequencing data. *Nature methods.* June 2013; 10(6):563-569.

100. Li L, Stoeckert C J, Jr., Roos D S. OrthoMCL: identification of ortholog groups for eukaryotic genomes. *Genome Res.* September 2003; 13(9):2178-2189.

101. Moreno-Hagelsieb G, Latimer K. Choosing BLAST options for better detection of orthologs as reciprocal best hits. *Bioinformatics.* Feb. 1, 2008; 24(3):319-324.

102. Enright A J, Van Dongen S, Ouzounis C A. An efficient algorithm for large-scale detection of protein families. *Nucleic Acids Res.* Apr. 1, 2002; 30(7):1575-1584.

103. Heap J T, Kuehne S A, Ehsaan M, et al. The ClosTron: Mutagenesis in *Clostridium* refined and streamlined. *J. Microbiol. Methods.* January 2010; 80(1):49-55.

104. Heap J T, Pennington O J, Cartman S T, Carter G P, Minton N P. The ClosTron: a universal gene knock-out system for the genus *Clostridium*. *J. Microbiol. Methods.* September 2007; 70(3): 452-464.

105. Heap J T, Pennington O J, Cartman S T, Minton N P. A modular system for *Clostridium* shuttle plasmids. *J. Microbiol. Methods.* July 2009; 78(1):79-85.

106. Perutka J, Wang W, Goerlitz D, Lambowitz A M. Use of computer-designed group II introns to disrupt *Escherichia coli* DExH/D-box protein and DNA helicase genes. *J. Mol. Biol.* Feb. 13, 2004; 336(2):421-439.

107. Moon C, VanDussen KL, Miyoshi H, Stappenbeck T S. Development of a primary mouse intestinal epithelial cell monolayer culture system to evaluate factors that modulate IgA transcytosis. *Mucosal. Immunol.* July 2014; 7(4): 818-828.

108. Zaleznik D F, Finberg R W, Shapiro M E, Onderdonk A B, Kasper D L. A soluble suppressor T cell factor protects against experimental intraabdominal abscesses. *J. Clin. Invest.* March 1985; 75(3):1023-1027.

109. Paoletti L C, Wessels M R, Michon F, DiFabio J, Jennings H J, Kasper D L. Group B *Streptococcus* type II polysaccharide-tetanus toxoid conjugate vaccine. *Infect. Immun.* October 1992; 60(10):4009-4014.
110. Sebastian S, Pinkham J T, Lynch J G, et al. Cellular and humoral immunity are 4synergistic in protection against types A and B *Francisella tularensis. Vaccine.* Jan. 22, 2009; 27(4):597-605.
111. Wessels M R, Paoletti L C, Kasper D L, et al. Immunogenicity in animals of a polysaccharide-protein conjugate vaccine against type III group B *Streptococcus. J. Clin. Invest.* November 1990; 86(5):1428-1433.
112. Zhang J P, Wang Q, Smith T R, Hurst W E, Sulpizio T. Endotoxin removal using a synthetic adsorbent of crystalline calcium silicate hydrate. *Biotechnol. Prog.* July-August 2005; 21(4). 1220-1225
113. An D, Oh S F, Olszak T, et al. Sphingolipids from a symbiotic microbe regulate homeostasis of host intestinal natural killer T cells. *Cell.* Jan. 16, 2014; 156(1-2):123-133.
114. Mazmanian S K, Liu C H, Tzianabos A O, Kasper D L. An immunomodulatory molecule of symbiotic bacteria directs maturation of the host immune system. *Cell.* Jul. 15, 2005; 122(1): 107-118.
115. Tzianabos A O, Onderdonk A B, Rosner B, Cisneros R L, Kasper D L. Structural features of polysaccharides that induce intra-abdominal abscesses. *Science.* Oct. 15, 1993; 262(5132):416-419.
116. Tzianabos A O, Onderdonk A B, Smith R S, Kasper D L. Structure-function relationships for polysaccharide-induced intra-abdominal abscesses. *Infect. Immun.* August 1994; 62(8):3590-3593.
117. Tzianabos A O, Pantosti A, Baumann H, Brisson J R, Jennings H J, Kasper D L. The capsular polysaccharide of *Bacteroides fragilis* comprises two ionically linked polysaccharides. *J. Biol. Chem.* Sep. 5, 1992; 267(25):18230-18235.
118. van Pijkeren J P, Britton R A. High efficiency recombineering in lactic acid bacteria. *Nucleic Acids Res.* May 2012; 40(10):e76.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of increasing the levels of a Reg3 peptide in a subject in need thereof, comprising administering to the subject bacteria strain *Ruminococcus gnavus, Lactobacillus reuteri* or a combination thereof in an amount effective to increase the level of Reg3 peptide in the subject.

2. The method of claim 1, wherein the Reg3 peptide is Reg3a, Reg3γ, or Reg3β.

3. The method of claim 1, wherein the subject has an inflammatory condition.

4. The method of claim 1, wherein the subject has a bacterial infection.

5. The method of claim 4, wherein the bacterial infection is a gram-negative or gram-positive bacterium.

6. The method of claim 5, wherein the bacteria is gram positive and selected from the group consisting of an enterococci infection, a vancomycin-resistant enterococci (VRC) infection, a *Clostridium difficile* infection, a *Staphylococcus aureus* infection, a methicillin-resistant *Staphylococcus aureus* (MRSA) infection, and a combination thereof.

7. The method of claim 4, wherein the bacterial infection is caused by an antibiotic resistant pathogen.

8. The method of claim 1, wherein the *Ruminococcus gnavus, Lactobacillus reuteri* or combination thereof is in a composition formulated for oral administration or rectal administration.

9. The method of claim 1, wherein the *Ruminococcus gnavus, Lactobacillus reuteri*, or combination thereof is formulated for topical or inhalant administration.

10. The method of claim 1, wherein the *Ruminococcus gnavus, Lactobacillus reuteri*, or combination thereof are live, replication competent bacteria.

11. The method of claim 1, wherein the *Ruminococcus gnavus, Lactobacillus reuteri*, or combination thereof are not live, replication competent bacteria.

12. The method of claim 11, wherein the *Ruminococcus gnavus, Lactobacillus reuteri*, or combination thereof is in the form of a bacterial lysate.

13. The method of claim 1, wherein the Reg3 is Reg3γ and increases the stem cell proliferation within the gut of the subject.

* * * * *